US007943328B1

(12) United States Patent
Lois et al.

(10) Patent No.: US 7,943,328 B1
(45) Date of Patent: May 17, 2011

(54) METHOD AND SYSTEM FOR ASSISTING IN DIAGNOSING IRRITABLE BOWEL SYNDROME

(75) Inventors: Augusto Lois, San Diego, CA (US);
Bruce Neri, Carlsbad, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 777 days.

(21) Appl. No.: 11/679,149

(22) Filed: Feb. 26, 2007

Related U.S. Application Data

(60) Provisional application No. 60/921,486, filed on Mar. 3, 2006.

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 530/300; 530/350

(58) Field of Classification Search .................. None
See application file for complete search history.

(56) References Cited

U.S. PATENT DOCUMENTS

| | | | |
|---|---|---|---|
| 5,750,355 A | 5/1998 | Targan et al. |
| 5,830,675 A | 11/1998 | Targan et al. |
| 5,858,688 A | 1/1999 | Haskill et al. |
| 6,074,835 A | 6/2000 | Braun et al. |
| 6,218,129 B1 | 4/2001 | Walsh et al. |
| 6,630,444 B1 | 10/2003 | Schwartz et al. |
| 6,656,474 B1 | 12/2003 | Cedarbaum |
| 6,986,995 B2 | 1/2006 | Rose et al. |
| 7,048,906 B2 | 5/2006 | Lin et al. |
| 7,138,237 B1 | 11/2006 | Targan et al. |
| 7,192,724 B2 | 3/2007 | Boone et al. |
| 2002/0025348 A1 | 2/2002 | Basu et al. |
| 2002/0052007 A1 | 5/2002 | Chang et al. |
| 2002/0168698 A1 | 11/2002 | Boone et al. |
| 2003/0077246 A1 | 4/2003 | Welcher et al. |
| 2003/0082652 A1 | 5/2003 | Holten-Andersen et al. |
| 2003/0091549 A1 | 5/2003 | Collins et al. |
| 2003/0124617 A1 | 7/2003 | Gram et al. |
| 2003/0133875 A1 | 7/2003 | Kelly |
| 2003/0143548 A1 | 7/2003 | Camilleri et al. |
| 2003/0153495 A1 | 8/2003 | Lichenstein et al. |
| 2003/0157061 A1 | 8/2003 | Bennett |
| 2003/0211106 A1 | 11/2003 | Tornetta et al. |
| 2003/0215450 A1 | 11/2003 | Blake et al. |
| 2004/0043931 A1 | 3/2004 | Hersberg et al. |
| 2004/0077020 A1 | 4/2004 | Mannick et al. |
| 2004/0106778 A1 | 6/2004 | Fagan et al. |
| 2004/0122787 A1 | 6/2004 | Avinash et al. |
| 2004/0137074 A1 | 7/2004 | Vidal et al. |
| 2004/0213788 A1 | 10/2004 | Sweet et al. |
| 2004/0229783 A1 | 11/2004 | Pothoulakis et al. |
| 2004/0235960 A1 | 11/2004 | Burns et al. |
| 2005/0004155 A1 | 1/2005 | Boyd et al. |
| 2005/0009766 A1 | 1/2005 | Brantl |
| 2005/0031583 A1 | 2/2005 | Grewal |
| 2005/0065327 A1 | 3/2005 | Monk et al. |
| 2005/0100531 A1 | 5/2005 | Bienenstock |
| 2005/0107399 A1 | 5/2005 | Boman et al. |
| 2005/0130189 A1 | 6/2005 | Pasricha et al. |
| 2005/0136495 A1 | 6/2005 | Boone et al. |
| 2005/0187176 A1 | 8/2005 | Bates et al. |
| 2005/0220909 A1 | 10/2005 | Theoharides |
| 2005/0282840 A1 | 12/2005 | Ross et al. |
| 2006/0014224 A1 | 1/2006 | Brunner et al. |
| 2006/0058365 A1 | 3/2006 | Kohn et al. |
| 2006/0079442 A1 | 4/2006 | Ilan et al. |
| 2006/0121015 A1 | 6/2006 | Collins et al. |
| 2006/0189528 A1 | 8/2006 | Roberts et al. |
| 2006/0211752 A1 | 9/2006 | Kohn et al. |
| 2006/0217307 A1 | 9/2006 | Takashi et al. |
| 2006/0233743 A1 | 10/2006 | Kelly |
| 2006/0258604 A1 | 11/2006 | Strober et al. |
| 2006/0275210 A1 | 12/2006 | Rosen et al. |
| 2007/0003518 A1 | 1/2007 | Atkinson et al. |
| 2007/0015773 A1 | 1/2007 | Bergeron et al. |
| 2007/0020660 A1 | 1/2007 | Burczynski et al. |
| 2007/0269804 A1 | 11/2007 | Liew et al. |
| 2008/0085524 A1 | 4/2008 | Lois |
| 2008/0166719 A1 | 7/2008 | Lois |
| 2010/0094560 A1 | 4/2010 | Lois et al. |
| 2010/0222228 A1 | 9/2010 | Thielemans et al. |

FOREIGN PATENT DOCUMENTS

EP 1 439 393 A2 7/2004

(Continued)

OTHER PUBLICATIONS

U.S. Appl. No. 11/565,544, Lois et al.
Farrell, R.J., "Epidermal Growth Factor for Ulcerative Colitis," *The New England Journal of Medicine*, Jul. 24, 2003, vol. 349, No. 4, pp. 395-397.
Katsuta, T. et al., "Interleukin-8 and SDF1-α mRNA Expression in Colonic Biopsies From Patients With Inflammatory Bowel Disease," *The American Journal of Gastroenterology*, 2000, vol. 95, No. 11, pp. 3157-3164.
Nielsen, O.H. et al., "Intestinal Interleukin-8 Concentration and Gene Expression in Inflammatory Bowel Disease," *Scand. J. Gastroenterol.*, 1997, vol. 32, pp. 1028-1034.
Nielsen, O.H. et al., "Rectal Dialysate and Fecal Concentrations of Neutrophil Gelatinase- , Associated Lipocalin, Interleukin-8, and Tumor Necrosis Factor-α in Ulcerative Colitis," *The American Journal of Gastroenterology*, 1999, vol. 94, No. 10, pp. 2923-2928.

(Continued)

*Primary Examiner* — Lisa V Cook
(74) *Attorney, Agent, or Firm* — Kilpatrick, Townsend & Stockton LLP

(57) ABSTRACT

The present invention provides methods, systems, and code for accurately classifying or diagnosing a sample from an individual as an IBS sample. The methods and systems of the present invention are useful for ruling out one or more diseases or disorders that share a similar clinical presentation as IBS followed by identifying (i.e., ruling in) IBS using statistical algorithm(s) and/or empirical data. In particular, the methods and systems of the present invention use a first combination of learning statistical classifier systems to rule out IBD with an accuracy of greater than about 90% and a second combination of learning statistical classifier systems to rule in IBS in a non-IBD sample with an accuracy of greater than about 80%.

20 Claims, 4 Drawing Sheets

FOREIGN PATENT DOCUMENTS

| | | |
|---|---|---|
| EP | 1 439 393 A3 | 7/2004 |
| WO | WO 99/64627 A2 | 12/1999 |
| WO | WO 00/00608 A2 | 1/2000 |
| WO | WO 00/00608 A3 | 1/2000 |
| WO | WO 00/41707 A2 | 7/2000 |
| WO | WO 00/41707 A3 | 7/2000 |
| WO | WO 01/11334 A2 | 2/2001 |
| WO | WO 01/11334 A3 | 2/2001 |
| WO | WO 03/029423 A2 | 4/2003 |
| WO | WO 03/029423 A3 | 4/2003 |
| WO | WO 03/068170 A2 | 8/2003 |
| WO | WO 03/087830 A2 | 10/2003 |
| WO | WO 03/087830 A3 | 10/2003 |
| WO | WO 2004/009797 A2 | 1/2004 |
| WO | WO 2004/009797 A3 | 1/2004 |
| WO | WO 2004/022727 A1 | 3/2004 |
| WO | WO 2004/085677 A2 | 10/2004 |
| WO | WO 2004/085677 A3 | 10/2004 |
| WO | WO 2004/096853 A1 | 11/2004 |
| WO | WO 2005/009339 A2 | 2/2005 |
| WO | WO 2005/009339 A3 | 2/2005 |
| WO | WO 2005/029091 A2 | 3/2005 |
| WO | WO 2005/029091 A3 | 3/2005 |
| WO | WO 2005/068655 A2 | 7/2005 |
| WO | WO 2005/068655 A3 | 7/2005 |
| WO | WO 2006/048698 A1 | 5/2006 |
| WO | WO 2006/057027 A1 | 6/2006 |
| WO | WO 2006/085075 A2 | 8/2006 |
| WO | WO 2006/085075 A3 | 8/2006 |
| WO | WO 2007/011674 A2 | 1/2007 |

OTHER PUBLICATIONS

Seth, R. et al., "Correlation Between Interleukin-8 (IL8) mRNA Levels and Histological Findings in Inflammatory Bowel Disease," Jan. 4-6, 1995, p. 101A (Meeting Abstract).

Restriction Requirement in U.S. Appl. No. 11/838,810 dated Apr. 8, 2010, pp. 1-11.

Restriction Requirement in U.S. Appl. No. 11/838,810 dated Jul. 15, 2010, pp. 1-7.

Office Action in U.S. Appl. No. 11/838,810 dated Oct. 27, 2010, pp. 1-21.

Restriction Requirement in U.S. Appl. No. 11/841,660 dated May 6, 2010, pp. 1-11.

Office Action in U.S. Appl. No. 11/841,660, dated Oct. 13, 2010, pp. 1-16.

Communication Relating to the Results of the Partial International Search mailed on Jul. 17, 2008, for PCT Application No. PCT/US2007/075976, filed on Aug. 15, 2007, 3 pages.

Barbara, G. et al.; "New pathophysiological mechanisms in irritable bowel syndrome," *Ailment Pharmacol Ther.*; 2004; vol. 20, Suppl. 2, pp. 1-9.

Curnow, S.J. et al., "Multiplex Bead Immunoassay Analysis of Aqueous Humor Reveals Distinct Cytokine Profiles in Uveitis," *Investigative Ophthalmology & Visual Science*, Nov. 2005, vol. 46, No. 11, pp. 4251-4259.

Delafoy, L., et al., "Interactive involvement of brain derived neurotrophic factor, nerve growth factor, and calcitonin gene related peptide in colonic hypersensitivity in the rat," *Gut*, 2006; vol. 55, pp. 940-945.

Dinan, T.G. et al., "Hypothalamic-Pituitary-Gut Axis Dysregulation in Irritable Bowel Syndrome: Plasma Cytokines as a Potential Biomarker?" *Gastroenterology*, Feb. 1, 2006, vol. 130, No. 2, pp. 304-311.

Drossman, D.A., "What Does the Future Hold for Irritable Bowel Syndrome and the Functional Gastrointestinal Disorders?" *Journal of Clinical Gastroenterology*, May/Jun. 2005, vol. 39, No. 4, Suppl. 3, pp. S251-S256.

Kane, S.V., "Fecal Lactoferrin Is a Sensitive and Specific Marker in Identifying Intestinal Inflammation," *American Journal of Gastroenterology*, 2003, vol. 98, No. 6, pp. 1309-1314.

Thierry, P. et al., "Impact of Fatigue in Irritable Bowel syndrome: Role of Plasma Leptin," *Gastroenterology AGA Abstracts*, Apr. 1, 2005, vol. 128, No. 4, Suppl. 2, Abstract No. W1488, p. A-623.

Wiley, S.R. et al., "TWEAK, a Member of the TNF Superfamily, is a Multifunctional Cytokine That Binds the TweakR/Fn14 Receptor," *Cytokine & Growth Factor Reviews*, Jan. 1, 2003, vol. 14, pp. 241-249.

METHOD AND SYSTEM FOR ASSISTING IN DIAGNOSING IRRITABLE BOWEL SYNDROME

CROSS-REFERENCES TO RELATED APPLICATIONS

The present application claims priority to U.S. application Ser. No. 11/368,285, filed Mar. 3, 2006, which has been converted to a U.S. Provisional Application No. 60/921,486, Mar. 3, 2006 which is herein incorporated by reference in its entirety for all purposes.

BACKGROUND OF THE INVENTION

Irritable bowel syndrome (IBS) is the most common of all gastrointestinal disorders, affecting 10-20% of the general population and accounting for more than 50% of all patients with digestive complaints. However, studies suggest that only about 10% to 50% of those afflicted with IBS actually seek medical attention. Patients with IBS present with disparate symptoms such as, for example, abdominal pain predominantly related to defecation, alternating diarrhea and constipation, abdominal distention, gas, and excessive mucus in the stool. More than 40% of IBS patients have symptoms so severe that they have to take time off from work, curtail their social life, avoid sexual intercourse, cancel appointments, stop traveling, take medication, and even stay confined to their house for fear of embarrassment. The estimated health care cost of IBS in the United States is $8 billion per year (Talley et al., *Gastroenterol.*, 109, 1736, (1995)).

The precise pathophysiology of IBS is not well understood. Nevertheless, there is a heightened sensitivity to visceral pain perception, known as peripheral sensitization. This sensitization involves a reduction in the threshold and an increase in the gain of the transduction processes of primary afferent neurons, attributable to a variety of mediators including monoamines (e.g., catecholamines and indoleamines), substance P, and variety of cytokines and prostanoids such as E-type prostaglandins (see, e.g., Mayer et al., *Gastroenterol.*, 107:271-293 (1994)). Also implicated in the etiopathology of IBS is intestinal motor dysfunction, which leads to abnormal handling of intraluminal contents and/or gas (see, e.g., Kellow et al., *Gastroenterol.*, 92:1885-1893 (1987); Levitt et al., *Ann. Int. Med.*, 124:422-424 (1996)). Psychological factors may also contribute to IBS symptoms appearing in conjunction with, if not triggered by, disturbances including depression and anxiety (see, e.g., Drossman et al., *Gastroenterol. Int.*, 8:47-90 (1995)).

Although the etiology of IBS is not fully characterized, the medical community has developed a consensus definition and criteria, known as the Rome II criteria, to aid in the diagnosis of IBS based upon patient history. The Rome II criteria requires three months of continuous or recurrent abdominal pain or discomfort over a one-year period that is relieved by defecation and/or associated with a change in stool frequency or consistency as well as two or more of the following: altered stool frequency, altered stool form, altered stool passage, passage of mucus, or bloating and abdominal distention. The absence of any structural or biochemical disorders that could be causing the symptoms is also a necessary condition. As a result, the Rome II criteria can be used only when there is a substantial patient history and is reliable only when there is no abnormal intestinal anatomy or metabolic process that would otherwise explain the symptoms.

It is well documented that diagnosing a patient as having IBS can be challenging due to the similarity in symptoms between IBS and other diseases or disorders. In fact, because the symptoms of ms are similar or identical to the symptoms of so many other intestinal illnesses, it can take years before a correct diagnosis is made. For example, patients who have inflammatory bowel disease (IBD) but who exhibit mild signs and symptoms such as bloating, diarrhea, constipation, and abdominal pain may be difficult to distinguish from patients with ms. As a result, the similarity in symptoms between IBS and IBD renders rapid and accurate diagnosis difficult. The difficulty in differentially diagnosing IBS and IBD hampers early and effective treatment of these diseases. Unfortunately, rapid and accurate diagnostic methods for definitively distinguishing IBS from other intestinal diseases or disorders presenting with similar symptoms are currently not available. The present invention satisfies this need and provides related advantages as well.

BRIEF SUMMARY OF THE INVENTION

The present invention provides methods, systems, and code for accurately classifying or diagnosing a sample from an individual as an IBS sample. The methods and systems of the present invention are useful for ruling out one or more diseases or disorders that share a similar clinical presentation as IBS followed by identifying (i.e., ruling in) IBS using statistical algorithm(s) and/or empirical data. In particular, the methods, systems and code of the present invention use a first combination of learning statistical classifier systems to rule out IBD with an accuracy of greater than about 90%. In addition to ruling out IBD, the present invention is useful for ruling out other diseases or disorders that share a similar clinical presentation as IBS. These include, for example, Celiac disease (CD), intestinal inflammation, colorectal cancer, maldigestion, malabsorption, endometriosis, and the like. In certain aspects, the present invention uses a second combination of learning statistical classifier systems to rule in IBS in a non-IBD sample with an accuracy of greater than about 80%.

In one aspect, the present invention provides a method for classifying whether a sample from an individual is associated with irritable bowel syndrome (IBS), the method comprising:
(a) determining the presence or level of at least one inflammatory bowel disease (IBD) marker in the sample;
(b) classifying the sample as a non-IBD sample or as an IBD sample using a first statistical algorithm based upon the presence or level of the at least one IBD marker; and
if the sample is classified as a non-IBD sample,
(c) classifying the non-IBD sample as an IBS sample or as a non-IBS sample using a second statistical algorithm based upon the presence or level of the at least one IBD marker.

In another aspect, the present invention provides a computer-readable medium including code for controlling one or more processors to classify whether a sample from an individual is associated with irritable bowel syndrome (IBS), the code including instructions to:
(a) apply a first statistical process to a data set indicating the presence or level of at least one inflammatory bowel disease (IBD) marker in the sample to produce a first statistically derived decision classifying the sample as a non-IBD sample or as an IBD sample based upon the presence or level of the at least one IBD marker; and
if the sample is classified as a non-IBD sample,
(b) apply a second statistical process to the data set to produce a second statistically derived decision classifying the non-IBD sample as an IBS sample or as a non-IBS sample based upon the presence or level of the at least one IBD marker.

In yet another aspect, the present invention provides a system for diagnosing irritable bowel syndrome (IBS) in a sample from an individual, the system comprising:
(a) a data acquisition module configured to produce a data set indicating the presence or level of at least one inflammatory bowel disease (IBD) marker in the sample; and
(b) a data processing module configured to process the data set to: classify the sample as a non-MD sample or as an IBD sample using a first statistical algorithm based upon the presence or level of the at least one IBD marker; and diagnose IBS in the non-IBD sample using a second statistical algorithm based upon the presence or level of the at least one IBD marker; and
(c) a display module configured to display output data produced by the first and/or the second statistical algorithm.

In a further aspect, the present invention provides a system for classifying whether a sample from an individual is associated with irritable bowel syndrome (IBS), the system comprising:
(a) a data acquisition module configured to produce a data set indicating the presence or level of at least one inflammatory bowel disease (IBD) marker in the sample; and
(b) a data processing module configured to process the data set by:
applying a first statistical process to the data set to produce a first statistically derived decision classifying the sample as a non-IBD sample or as an IBD sample based upon the presence or level of the at least one IBD marker; and
if the sample is classified as a non-IBD sample, apply a second statistical process to the data set to produce a second statistically derived decision classifying the non-IBD sample as an IBS sample or as a non-IBS sample based upon the presence or level of the at least one IBD marker; and
(c) a display module configured to display the first and/or the second statistically derived decision.

Other objects, features, and advantages of the present invention will be apparent to one of skill in the art from the following detailed description and figures.

DETAILED DESCRIPTION OF THE INVENTION

I. Introduction

Diagnosing a patient as having irritable bowel syndrome (IBS) can be challenging due to the similarity in symptoms between IBS and other diseases or disorders. For example, patients who have inflammatory bowel disease (IBD) but who exhibit mild signs and symptoms such as bloating, diarrhea, constipation, and abdominal pain may be difficult to distinguish from patients with IBS. As a result, the similarity in symptoms between IBS and IBD renders rapid and accurate diagnosis difficult and hampers early and effective treatment of these diseases.

The present invention is based, in part, upon the surprising discovery that the accuracy of classifying a sample from an individual as an IBS sample can be substantially improved by first excluding (i.e., ruling out) one or more diseases or disorders that share a similar clinical presentation as IBS followed by identifying (i.e., ruling in) IBS using statistical algorithm(s) and/or empirical data. In particular, the methods of the present invention advantageously use a first combination of learning statistical classifier systems to rule out IBD with an accuracy of greater than about 90% and a second combination of learning statistical classifier systems to rule in IBS in a non-IBD sample with an accuracy of greater than about 80%.

Figure 1:
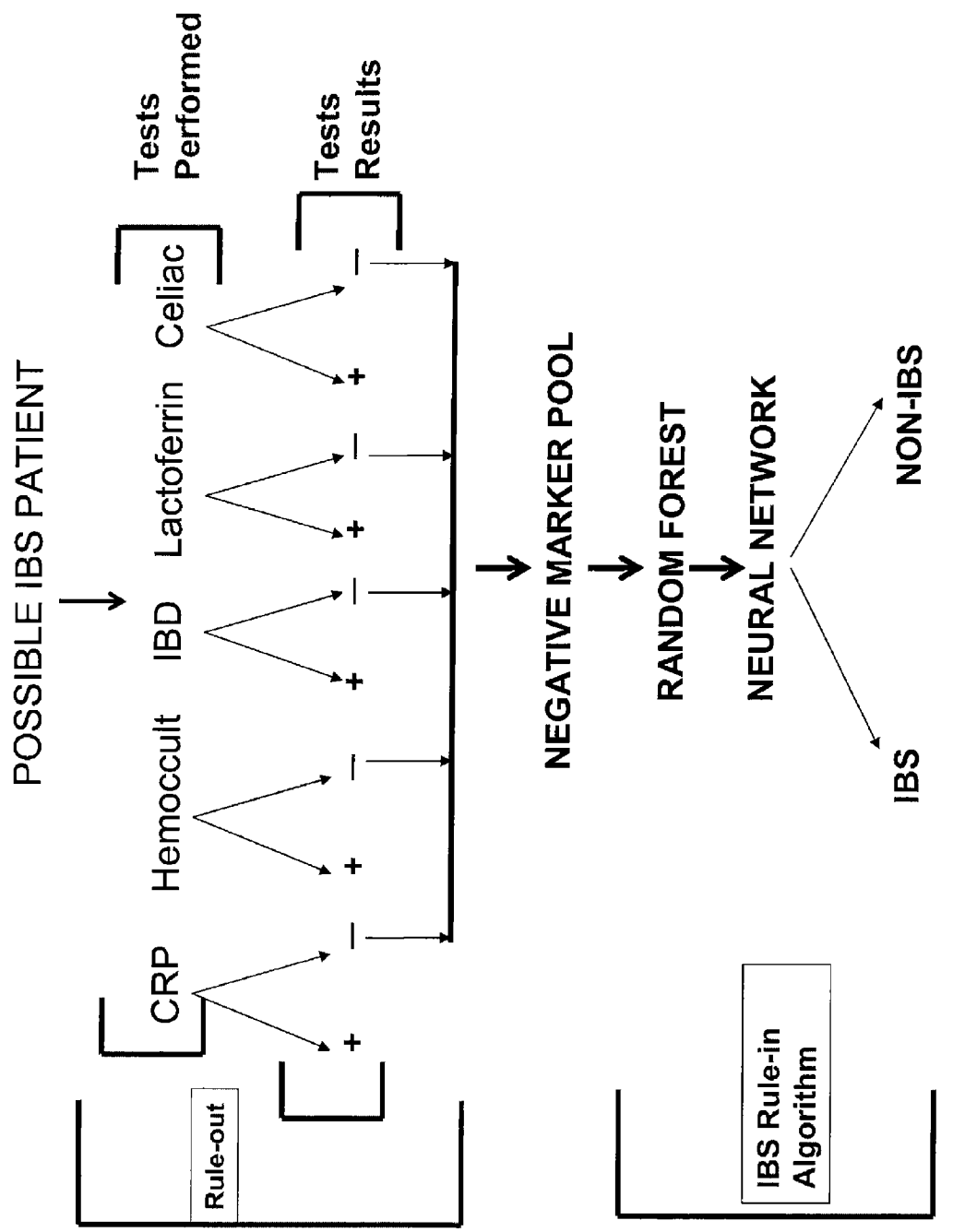
FIG. 1 illustrates one embodiment of the present invention using a "rule-out/rule-in" approach for classifying a sample as an IBS sample.

For example, FIG. 1 illustrates one embodiment of the present invention using a "rule-out/rule-in" approach for classifying a sample as an IBS sample. A panel of tests is first performed on a sample (e.g., serum, stool, etc.) from a patient suspected of having IBS to rule out diseases or disorders with similar symptoms as IBS. If the sample is negative for all of these diseases or disorders, IBS is then ruled in using a combination of random forest and neural network learning statistical classifier systems. As a result, the present invention provides rapid and accurate methods for definitively distinguishing IBS from other intestinal diseases or disorders presenting with IBS-like symptoms. Various systems and codes for carrying out the classification methods of the present invention are also provided.

II. Definitions

As used herein, the following terms have the meanings ascribed to them unless specified otherwise.

The term "classifying" means to associate or categorize a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model or template against which the features of an unknown sample are compared, in order to classify the unknown disease state of the sample. In certain instances, classifying the sample is akin to diagnosing the disease state of the sample.

The term "irritable bowel syndrome" or "IBS" refers to a group of functional bowel disorders characterized by one or more symptoms including abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). There are also various clinical subtypes of IBS, such as post-infectious IBS (IBS-PI).

The term "sample" refers to any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-86

(1997)). One skilled in the art understands that samples such as serum samples can be diluted prior to the analysis of marker levels.

The term "marker" refers to any biochemical marker, serological marker, genetic marker, or other clinical or echographic characteristic that can be used to rule out one or more diseases or disorders associated with IBS-like symptoms in a sample from an individual (e.g., an individual suspected of having IBS). The term also encompasses any marker that can be used to rule in IBS in those samples that have first been ruled out for diseases or disorders associated with IBS-like symptoms. Non-limiting examples of markers suitable for use in the present invention are described below and include inflammatory bowel disease (IBD) markers, irritable bowel syndrome (IBS) markers, Celiac disease (CD) markers, C-reactive protein (CRP), lactoferrin, calprotectin, hemoglobin, and the like. One skilled in the art will know of additional markers suitable for use in the present invention.

As used herein, the term "substantially the same amino acid sequence" refers to an amino acid sequence that is similar but not identical to the naturally-occurring amino acid sequence. For example, an amino acid sequence, i.e., polypeptide, that has substantially the same amino acid sequence as an I2 protein can have one or more modifications such as amino acid additions, deletions, or substitutions relative to the amino acid sequence of the naturally-occurring I2 protein, provided that the modified polypeptide retains substantially at least one biological activity of I2 such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "therapeutically effective amount or dose" refers to a dose of a drug that is capable of achieving a therapeutic effect in a subject in need thereof. For example, a therapeutically effective amount of a drug useful for treating IBS can be the amount that is capable of preventing or relieving one or more symptoms associated with IBS. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

III. Description of the Embodiments

The present invention provides methods, systems, and code for accurately classifying or diagnosing a sample from an individual as an IBS sample. As a non-limiting example, the methods and systems of the present invention are particularly useful for ruling out one or more diseases or disorders that present with IBS-like symptoms followed by ruling in IBS using a combination of statistical algorithms and/or empirical data.

In one aspect, the present invention provides a method for classifying whether a sample from an individual is associated with irritable bowel syndrome (IBS), the method comprising:

(a) determining the presence or level of at least one inflammatory bowel disease (IBD) marker in the sample;

(b) classifying the sample as a non-IBD sample or as an IBD sample using a first statistical algorithm based upon the presence or level of the at least one IBD marker; and if the sample is classified as a non-IBD sample, (c) classifying the non-IBD sample as an IBS sample or as a non-IBS sample using a second statistical algorithm based upon the presence or level of the at least one IBD marker.

Examples of IBD markers suitable for use in the present invention include, but are not limited to, an anti-neutrophil cytoplasmic antibody (ANCA), an anti-*Saccharomyces cerevisiae* immunoglobulin A antibody (ASCA-IgA), an anti-*Saccharomyces cerevisiae* immunoglobulin G antibody (ASCA-IgG), an anti-outer membrane protein C (anti-OmpC) antibody, an anti-flagellin antibody, an anti-I2 antibody, a perinuclear anti-neutrophil cytoplasmic antibody (pANCA), and a combination thereof. In certain instances, the presence or level of other IBD markers such as, for example, elastase, lactoferrin, or calprotectin can be determined.

In another embodiment, the method for classifying whether a sample from an individual is associated with IBS comprises determining the presence or level of at least two, three, four, five, six, or more IBD markers. For example, the method can comprise determining the presence or level of ASCA-IgG and anti-OmpC antibody in a sample. Preferably, the method comprises determining the presence or level of ANCA, ASCA-IgG, and anti-OmpC antibody in a serum sample. In certain instances, the first and second statistical algorithms are based upon the presence or level of different IBD markers. In certain other instances, the first and second statistical algorithms are based upon the presence or level of at least one, two, three, or more of the same MD markers. Such statistical algorithms can further comprise at least one, two, three, or more different IBD markers.

In yet another embodiment, the method further comprises determining the presence or level of at least one IBS marker in the sample and classifying the non-IBD sample as an IBS sample or as a non-IBS sample using a second statistical algorithm based upon the presence or level of the at least one IBD marker and the at least one IBS marker. Examples of IBS markers suitable for use in the present invention include, but are not limited to, polymorphisms in the serotonin reuptake transporter (SERT) gene, SERT mRNA level, mucosal SERT expression level, tryptophan hydroxylase-1 expression level, tryptophan hydroxylase mRNA level, 5-hydroxytryptamine (5-HT) level, a lactulose breath test, and combinations thereof.

In still yet another embodiment, the method further comprises ruling out at least one other disease or disorder selected from the group consisting of Celiac disease (CD), intestinal inflammation (e.g., acute inflammation, diverticulitis, ileal pouch-anal anastomosis, microscopic colitis, infectious diarrhea, and a combination thereof), lactase deficiency, cancer, a mechanical obstruction of the intestine, an enteric infection, ischemia, maldigestion, malabsorption, endometriosis, and a combination thereof. The at least one other disease or disorder can be ruled out prior to, concurrently with, or subsequent to step (b).

In certain instances, CD is ruled out based upon the presence or level of at least one CD marker in the sample. Examples of CD markers suitable for use in the present invention include, but are not limited to, an anti-gluten antibody, an anti-tissue transglutaminase (tTG) antibody, an anti-gluten/tTG complex antibody, an anti-protamine sulfate antibody, an anti-protamine sulfate/tTG complex antibody, an anti-endomysial antibody, an anti-actin antibody, an anti-reticulin antibody, an anti-zonulin antibody, an anti-ATP synthase β chain antibody, an anti-enolase α antibody, an anti jejunal antibody, zonulin, motilin, an interleukin, a human leukocyte antigen (HLA), prolactin, soluble CD163, and a combination thereof.

In certain other instances, intestinal inflammation is ruled out based upon the presence or level of C-reactive protein and/or lactoferrin and/or calprotectin in the sample. Intestinal inflammation, as well as ulcers, cancer, and hemorrhoids, can also be ruled out based upon the presence or level of blood in a stool sample such as fecal hemoglobin from the individual.

In another embodiment, the first statistical algorithm is a learning statistical classifier system. Examples of learning statistical classifier systems suitable for use in the present invention include, but are not limited to, a classification and regression tree, a neural network, a random forest, a support vector machine, a multilayer perceptron, a backpropagation network, a Levenberg-Marquardt algorithm, and a combination thereof. In certain instances, the learning statistical classifier system is a combination of at least two learning statistical classifier systems. Preferably, the combination of learning statistical classifier systems comprises a random forest and a neural network, e.g., used in tandem. As a non-limiting example, a random forest can first be used to generate a probability value based upon the presence or level of the at least one IBD marker, and a neural network can then be used to classify the sample as a non-IBD sample or as an IBD sample based upon the probability value and the presence or level of the at least one IBD marker. Example 6 below provides a description of hybrid models for ruling out IBD (i.e., classifying the sample as a non-IBD sample) that are derived from a combination of random forest and neural network classifier systems. Such hybrid models advantageously classify the sample as a non-IBD sample with a negative predictive value of at least about 95% (e.g., 97%) and/or an accuracy of at least about 90%.

In yet another embodiment, the second statistical algorithm is a learning statistical classifier system. Examples of learning statistical classifier systems suitable for use in the present invention are described above. In certain instances, the learning statistical classifier system is a combination of at least two learning statistical classifier systems. Preferably, the combination of learning statistical classifier systems comprises a random forest and a neural network or support vector machine, e.g., used in tandem. As a non-limiting example, a random forest can first be used to generate a probability value based upon the presence or level of the at least one IBD marker, and a neural network or support vector machine can then be used to classify IBS in the non-IBD sample based upon the probability value and the presence or level of the at least one IBD marker. Example 7 below provides a description of hybrid models for ruling in IBS (i.e., classifying IBS in the non-IBD sample) that are derived from a combination of random forest and neural network or support vector machine classifier systems. Such hybrid models advantageously classify the non-IBD sample as an IBS sample with a sensitivity of at least about 80% and/or an accuracy of at least about 80%.

In certain instances, the presence or level of the one or more IBD markers is determined using an immunoassay. A variety of antigens are suitable for use in detecting and/or determining the level of each IBD marker in an immunoassay such as an enzyme-linked immunosorbent assay (ELISA). Antigens specific for ANCA that are suitable for determining ANCA levels include, e.g., fixed neutrophils; unpurified or partially purified neutrophil extracts; purified proteins, protein fragments, or synthetic peptides such as histone H1, histone H1-like antigens, porin antigens, *Bacteroides* antigens, secretory vesicle antigens, or ANCA-reactive fragments thereof; and combinations thereof. Preferably, the level of ANCA is determined using fixed neutrophils. Antigens specific for ASCA, i.e., ASCA-IgA and/or ASCA-IgG, include, e.g., whole killed yeast cells such as *Saccharomyces* or *Candida* cells; yeast cell wall mannan such as phosphopeptidomannan (PPM); oligosaccharides such as oligomannosides; neoglycolipids; purified antigens; synthetic antigens; and combinations thereof. Antigens specific for anti-OmpC antibodies that are suitable for determining anti-OmpC antibody levels include, e.g., an OmpC protein, an OmpC polypeptide having substantially the same amino acid sequence as the OmpC protein, a fragment thereof such as an immunoreactive fragment thereof, and combinations thereof. Antigens specific for anti-I2 antibodies that are suitable for determining anti-I2 antibody levels include, e.g., an I2 protein, an I2 polypeptide having substantially the same amino acid sequence as the I2 protein, a fragment thereof such as an immunoreactive fragment thereof, and combinations thereof. Antigens specific for anti-flagellin antibodies that are suitable for determining anti-flagellin antibody levels include, e.g., a flagellin protein such as Cbir-1 flagellin, flagellin X, flagellin A, flagellin B, fragments thereof, and combinations thereof; a flagellin polypeptide having substantially the same amino acid sequence as the flagellin protein; a fragment thereof such as an immunoreactive fragment thereof; and combinations thereof.

In certain other instances, the presence or level of the one or more IBD markers is determined using an immunohistochemical assay. Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays. An immunofluorescence assay, for example, is particularly useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard. Preferably, the presence of pANCA is determined in a sample from the individual using DNase-treated, fixed neutrophils as described, e.g., in Example 5.

In another embodiment, the sample used for detecting or determining the presence or level of the at least one IBD marker is whole blood, plasma, serum, saliva, urine, stool (i.e., feces), tears, and any other bodily fluid, or a tissue sample (i.e., biopsy) such as a small intestine or colon sample. In a preferred embodiment, the sample is serum. In other preferred embodiments, the sample is plasma, urine, feces, or a tissue biopsy. In certain instances, the method of the present invention further comprises obtaining the sample from the individual prior to detecting or determining the presence or level of the at least one IBD marker in the sample.

In a further embodiment, the method of the present invention further comprises sending the IBS classification results to a clinician, e.g., a gastroenterologist or a general practitioner. In an additional embodiment, the method of the present invention provides a diagnosis in the form of a probability that the individual has IBS. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBS. In certain instances, the IBS is characterized by at least one symptom selected from the group consisting of abdominal pain, abdominal discomfort, change in bowel pattern, loose or more frequent bowel movements, diarrhea, constipation, and a combination thereof.

In an additional embodiment, the method of the present invention further comprises administering to the individual a therapeutically effective amount of a drug useful for treating one or more symptoms associated with IBS (i.e., an IBS drug) once the sample has been classified as an IBS sample. Suitable IBS drugs include, but are not limited to, serotonergic agents, antidepressants, chloride channel activators, guanylate cyclase agonists, antibiotics, opioids, neurokinin antagonists, antispasmodic or anticholinergic agents, belladonna alkaloids, barbiturates, free bases thereof, pharmaceutically acceptable salts thereof, derivatives thereof, analogs thereof, and combinations thereof. Other IBS drugs include bulking agents, dopamine antagonists, carminatives, tranquilizers, phenyloin, timolol, and diltiazem. Additionally, amino acids like glutamine and glutamic acid which regulate intestinal permeability by affecting neuronal or glial cell signaling can be administered to treat patients with IBS.

In another aspect, the present invention provides a computer-readable medium including code for controlling one or more processors to classify whether a sample from an individual is associated with irritable bowel syndrome (IBS), the code including instructions to:
 (a) apply a first statistical process to a data set indicating the presence or level of at least one inflammatory bowel disease (IBD) marker in the sample to produce a first statistically derived decision classifying the sample as a non-IBD sample or as an IBD sample based upon the presence or level of the at least one IBD marker; and
 if the sample is classified as a non-IBD sample,
 (b) apply a second statistical process to the data set to produce a second statistically derived decision classifying the non-IBD sample as an IBS sample or as a non-IBS sample based upon the presence or level of the at least one IBD marker.

In one embodiment, the first and second processes are implemented in different processors. Alternatively, the first and second processes are implemented in a single processor. In another embodiment, the first statistical process is a learning statistical classifier system. Examples of learning statistical classifier systems suitable for use in the present invention are described above. In certain instances, the learning statistical classifier system is a combination of at least two learning statistical classifier systems. Preferably, the combination of learning statistical classifier systems comprises a random forest and a neural network, e.g., used in tandem. In yet another embodiment, the second statistical process is a learning statistical classifier system. In certain instances, the learning statistical classifier system is a combination of at least two learning statistical classifier systems. Preferably, the combination of learning statistical classifier systems comprises a random forest and a neural network or support vector machine, e.g., used in tandem.

In yet another aspect, the present invention provides a system for diagnosing irritable bowel syndrome (IBS) in a sample from an individual, the system comprising:
 (a) a data acquisition module configured to produce a data set indicating the presence or level of at least one inflammatory bowel disease (IBD) marker in the sample; and
 (b) a data processing module configured to process the data set to: classify the sample as a non-IBD sample or as an IBD sample using a first statistical algorithm based upon the presence or level of the at least one IBD marker; and
 diagnose IBS in the non-IBD sample using a second statistical algorithm based upon the presence or level of the at least one IBD marker; and
 (c) a display module configured to display output data produced by the first and/or the second statistical algorithm.

In one embodiment, the first and/or second statistical algorithm is a learning statistical classifier system. Examples of learning statistical classifier systems suitable for use in the present invention are described above.

In a further aspect, the present invention provides a system for classifying whether a sample from an individual is associated with irritable bowel syndrome (IBS), the system comprising:
 (a) a data acquisition module configured to produce a data set indicating the presence or level of at least one inflammatory bowel disease (IBD) marker in the sample; and
 (b) a data processing module configured to process the data set by:
 applying a first statistical process to the data set to produce a first statistically derived decision classifying the sample as a non-IBD sample or as an IBD sample based upon the presence or level of the at least one IBD marker; and
 if the sample is classified as a non-IBD sample, apply a second statistical process to the data set to produce a second statistically derived decision classifying the non-IBD sample as an ms sample or as a non-IBS sample based upon the presence or level of the at least one IBD marker; and
 (c) a display module configured to display the first and/or the second statistically derived decision.

In one embodiment, the first and/or second statistical process is a learning statistical classifier system. Examples of learning statistical classifier systems suitable for use in the present invention are described above.

IV. Diseases and Disorders with IBS-Like Symptoms

A variety of structural or metabolic diseases and disorders can cause signs or symptoms that are similar to IBS. As non-limiting examples, patients with diseases and disorders such as inflammatory bowel disease (IBD), Celiac disease (CD), acute inflammation, diverticulitis, ileal pouch-anal anastomosis, microscopic colitis, infectious diarrhea, lactase deficiency, cancer (e.g., colorectal cancer), a mechanical obstruction of the small intestine or colon, an enteric infection, ischemia, maldigestion, malabsorption, endometriosis, and unidentified inflammatory disorders of the intestinal tract can present with abdominal discomfort associated with mild to moderate pain and a change in the consistency and/or frequency of stools that are similar to IBS. Additional IBS-like symptoms can include chronic diarrhea or constipation or an alternating form of each, weight loss, abdominal distention or bloating, and mucus in the stool.

Most IBD patients can be classified into one of two distinct clinical subtypes, Crohn's disease and ulcerative colitis. Crohn's disease is an inflammatory disease affecting the lower part of the ileum and often involving the colon and other regions of the intestinal tract. Ulcerative colitis is characterized by an inflammation localized mostly in the mucosa and submucosa of the large intestine. Patients suffering from these clinical subtypes of IBD typically have IBS-like symptoms such as, for example, abdominal pain, chronic diarrhea, weight loss, and cramping.

The clinical presentation of Celiac disease is also characterized by IBS-like symptoms such as abdominal discomfort associated with chronic diarrhea, weight loss, and abdominal distension. Celiac disease is an immune-mediated disorder of the intestinal mucosa that is typically associated with villous atrophy, crypt hyperplasia, and/or inflammation of the mucosal lining of the small intestine. In addition to the malabsorption of nutrients, individuals with Celiac disease are at risk for mineral deficiency, vitamin deficiency, osteoporosis, autoimmune diseases, and intestinal malignancies (e.g., lymphoma and carcinoma). It is thought that exposure to proteins such as gluten (e.g., glutenin and prolamine proteins which are present in wheat, rye, barley, oats, millet, triticale, spelt, and kamut), in the appropriate genetic and environmental context, is responsible for causing Celiac disease.

Other diseases and disorders characterized by intestinal inflammation that present with IBS-like symptoms include, for example, acute inflammation, diverticulitis, ileal pouch-anal anastomosis, microscopic colitis, and infectious diarrhea, as well as unidentified inflammatory disorders of the intestinal tract. Patients experiencing episodes of acute inflammation typically have elevated C-reactive protein (CRP) levels in addition to IBS-like symptoms. CRP is produced by the liver during the acute phase of the inflammatory process and is usually released about 24 hours post-commencement of the inflammatory process. Patients suffering from diverticulitis, ileal pouch-anal anastomosis, microscopic colitis, and infectious diarrhea typically have elevated fecal lactoferrin and/or calprotectin levels in addition to IBS-like symptoms. Lactoferrin is a glycoprotein secreted by mucosal membranes and is the major protein in the secondary granules of leukocytes. Leukocytes are commonly recruited to inflammatory sites where they are activated, releasing granule content to the surrounding area. This process increases the concentration of lactoferrin in the stool.

Increased lactoferrin levels are observed in patients with ileal pouch-anal anastomosis (i.e., a pouch is created following complete resection of colon in severe cases of Crohn's disease) when compared to other non-inflammatory conditions of the pouch, like irritable pouch syndrome. Elevated levels of lactoferrin are also observed in patients with diverticulitis, a condition in which bulging pouches (i.e., diverticula) in the digestive tract become inflamed and/or infected, causing severe abdominal pain, fever, nausea, and a marked change in bowel habits. Microscopic colitis is a chronic inflammatory disorder that is also associated with increased fecal lactoferrin levels. Microscopic colitis is characterized by persistent watery diarrhea (non-bloody), abdominal pain usually associated with weight loss, a normal mucosa during colonoscopy and radiological examination, and very specific histopathological changes. Microscopic colitis consists of two diseases, collagenous colitis and lymphocytic colitis. Collagenous colitis is of unknown etiology and is found in patients with long-term watery diarrhea and a normal colonoscopy examination. Both collagenous colitis and lymphocytic colitis are characterized by increased lymphocytes in the lining of the colon. Collagenous colitis is further characterized by a thickening of the sub-epithelial collagen layer of the colon. Infectious diarrhea is an illness that is also associated with increased fecal lactoferrin levels. Infectious diarrhea is usually caused by a bacterial or viral infection, with patients presenting with IBS-like symptoms such as diarrhea and abdominal pain. Increased lactoferrin levels are also observed in patients with IBD.

In addition to determining CRP and/or lactoferrin and/or calprotectin levels, diseases and disorders associated with intestinal inflammation can also be ruled out by detecting the presence of blood in the stool, such as fecal hemoglobin. Intestinal bleeding that occurs without the patient's knowledge is called occult or hidden bleeding. The presence of occult bleeding (e.g., fecal hemoglobin) is typically observed in a stool sample from the patient. Other conditions such as ulcers (e.g., gastric, duodenal), cancer (e.g., stomach cancer, colorectal cancer), and hemorrhoids can also present with IBS-like symptoms including abdominal pain and a change in the consistency and/or frequency of stools.

In addition, fecal calprotectin levels can also be assessed. Calprotectin is a calcium binding protein with antimicrobial activity derived predominantly from neutrophils and monocytes. Calprotectin has been found to have clinical relevance in cystic fibrosis, rheumatoid arthritis, IBD, colorectal cancer, HIV and other inflammatory diseases. Its level has been measured in serum/plasma, oral, cerebrospinal and synovial fluids, in urine and feces. Advantages of fecal calprotectin in GI disorders have been recognized: stable for 3-7 days at room temperature enabling sample shipping through regular mail, correlated to fecal alpha 1-antitrypsin in patients with Crohn's disease, and elevated in great majority of patients with gastrointestinal carcinomas and IBD. It was found that fecal calprotectin correlates well with endoscopic and histological gradings of disease activity in ulcerative colitis, and with fecal excretion of indium-111-labelled neutrophilic granulocytes, which is a standard of disease activity in IBD.

In view of the foregoing, it is clear that a wide array of diseases and disorders can cause IBS-like symptoms, thereby creating a substantial obstacle for definitively classifying a sample as an IBS sample. However, the present invention overcomes this limitation by first excluding (i.e., ruling out) those diseases and disorders that share a similar clinical presentation as IBS followed by identifying (i.e., ruling in) IBS in a sample using a statistical algorithm such as a learning statistical classifier system.

V. IBD Markers

A variety of inflammatory bowel disease (IBD) markers, such as biochemical markers, serological markers, genetic markers, or other clinical or echographic characteristics, are suitable for use in the statistical algorithms of the present invention for ruling out IBD, e.g., by classifying a sample from an individual suspected of having IBS as a non-IBD sample. The IBD markers described herein are also suitable for use in the statistical algorithms of the present invention for ruling in IBS, e.g., by classifying a non-IBD sample as an IBS sample. Examples of biochemical and serological IBD markers include, without limitation, ANCA (e.g., pANCA, cANCA, NSNA, SAPPA), ASCA-IgA, ASCA-IgG, anti-OmpC antibodies, anti-I2 antibodies, anti-flagellin antibodies, elastase, lactoferrin, calprotectin, and combinations thereof. An example of a genetic IBD marker is the NOD2/CARD15 gene. One skilled in the art will know of additional IBD markers suitable for use in the statistical algorithms of the present invention.

The determination of ANCA levels and/or the presence or absence of pANCA in a sample is particularly useful in the statistical algorithms of the present invention for ruling out IBD and/or ruling in IBS. As used herein, the term "anti-neutrophil cytoplasmic antibody" or "ANCA" refers to antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, *Bacteroides* antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

The determination of ASCA-IgA and/or ASCA-IgG levels in a sample is also particularly useful in the statistical algorithms of the present invention for ruling out IBD and/or ruling in IBS. As used herein, the term "anti-*Saccharomyces cerevisiae* immunoglobulin A" or "ASCA-IgA" refers to antibodies of the immunoglobulin A isotype that react specifically with *S. cerevisiae*. Similarly, the term "anti-*Saccharomyces cerevisiae* immunoglobulin G" or "ASCA-IgG" refers to antibodies of the immunoglobulin G isotype that react specifically with *S. cerevisiae*.

The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man $\beta$(1-2) D-Man $\beta$(1-2) D-Man $\beta$(1-2) D-Man-OR, D-Man $\alpha$(1-2) D-Man $\alpha$(1-2) D-Man $\alpha$(1-2) D-Man-OR, and D-Man $\alpha$(1-3) D-Man $\alpha$(1-2) D-Man $\alpha$(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction techniques known in the art, including, for example, by autoclaving, or can be obtained commercially (see, e.g., Lindberg et al., *Gut*, 33:909-913 (1992)). The acid-stable fraction of PPM is also useful in the statistical algorithms of the present invention (Sendid et al., *Clin. Diag. Lab. Immunol.*, 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man(1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

The determination of anti-OmpC antibody levels in a sample is also particularly useful in the statistical algorithms of the present invention for ruling out IBD and/or ruling in IBS. As used herein, the term "anti-outer membrane protein C antibody" or "anti-OmpC antibody" refers to antibodies directed to a bacterial outer membrane porin as described in, e.g., PCT Patent Publication No. WO 01/89361. The term "outer membrane protein C" or "OmpC" refers to a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display.

The determination of anti-I2 antibody levels in a sample is also particularly useful in the statistical algorithms of the present invention for ruling out IBD and/or ruling in IBS. As used herein, the term "anti-I2 antibody" refers to antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display.

The determination of anti-flagellin antibody levels in a sample is also particularly useful in the statistical algorithms of the present invention for ruling out IBD and/or ruling in IBS. As used herein, the term "anti-flagellin antibody" refers to antibodies directed to a protein component of bacterial flagella as described in, e.g., PCT Patent Publication No. WO 03/053220 and U.S. Patent Publication No. 20040043931. The term "flagellin" refers to a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis*, *Helicobacter mustelae*, *Helicobacter pylori*, *Butyrivibrio fibrisolvens*, and bacterium found in the cecum, by recombinant expression of a nucleic acid encoding a flagellin antigen, by synthetic means such as solution or solid phase peptide synthesis, or by using phage display.

VI. IBS Markers

A variety of irritable bowel syndrome (IBS) markers, such as biochemical markers, serological markers, genetic markers, or other clinical or echographic characteristics, are suitable for use in the statistical algorithms of the present invention for ruling in IBS, e.g., by classifying a non-IBD sample as an IBS sample. In certain embodiments, a non-IBD sample is classified as an IBS sample by ruling in IBS with the aid of at least one IBS marker. Examples of biochemical and serological IBD markers include, without limitation, polymorphisms in the serotonin reuptake transporter (SERT) gene, SERT mRNA level, mucosal SERT expression level, tryptophan hydroxylase-1 expression level, tryptophan hydroxylase mRNA level, 5-hydroxytryptamine (5-HT) level, a lactulose breath test, and combinations thereof. One skilled in the art will know of additional IBS markers suitable for use in the statistical algorithms of the present invention.

In one aspect, the IBS marker is a polymorphism in the serotonin reuptake transporter (SERT) gene. For example, polymorphisms in the serotonin reuptake transporter (SERT or 5-HTT) such as the promoter region of the SERT gene have effects on transcriptional activity, resulting in altered 5-HT reuptake efficiency. It was shown that with respect to the nine SERT polymorphisms, that a strong genotypic association was observed between the SERT-P deletion/deletion genotype and the IBS phenotype (see, Yeo A., *Gut*, 2004 October; 53(10):1396-9). In an alternative embodiment, SERT mRNA levels can be used as an IBS marker of the present invention. (see, Gershon, M D., *J. Clin. Gastroenterol.* 2005 May-June; 39(5 Suppl):S184-93), to aid in classifying IBS.

Further, as disclosed in Gershon, M D, *J. Clin Gastroenterol*, 2005 May-June; 39(4 Suppl 3):S184-93, mucosal SERT and tryptophan hydroxylase-1 expression are decreased in experimental inflammation, IBS-C, IBS-D, and ulcerative colitis. The loss of mucosal SERT may thus contribute to IBS pathogenesis, and thus mucosal SERT levels and/or tryptophan hydroxylase-1 expression levels can be used as IBS markers of the present invention.

In another aspect, the level of tryptophan hydroxylase mRNA is an IBS marker. For example, as disclosed in Coats M D., *Gastroenterology*, 2004 June; 126(7):1897-9, tryptophan hydroxylase mRNA was significantly reduced in IBS.

In still yet another aspect, the level of 5-hydroxytryptamine (5-HT) is a marker for IBS. For example, Dunlop, S. P. *Clin Gastroenterol Hepatol*. 2005 April; 3(4):349-57, disclosed that C-IBS patients show impaired postprandial 5-HT release whereas PI-IBS patients have higher peak levels of 5-HT. Thus, the levels of 5-HT can be correlated to IBS.

In certain other aspects, a lactulose breath test to measure methane, which is indicative of bacterial overgrowth, can be used to aid in ruling-in IBS patients.

Additional IBS markers include, but are not limited to, GNB3 polymorphisms, NCI1 polymorphisms, calprotectin, lactoferrin (and other fecal leukocytes), α2A and α2C adrenoreceptor and SERT polymorphisms, IL-10 polymorphisms, TNF-α polymorphisms, TGF-β1 polymorphisms, α-adrenergic receptors, g-proteins, 5-Ht2A gene polymorphisms, 5-HTT LPR polymorphisms, HT4 receptor polymorphisms, zonulin and the 33-mer (SEQ ID NO:1) below.

VII. CD Markers

A variety of Celiac disease (CD) markers, such as biochemical markers, serological markers, genetic markers, or other clinical or echographic characteristics, are suitable for use in the present invention for ruling out CD, e.g., by classifying a sample from an individual suspected of having IBS as a non-CD sample.

Examples of biochemical and serological CD markers include, without limitation, antibody markers such as anti-gluten antibodies (e.g., anti-gliadin antibodies), anti-tissue transglutaminase (tTG) antibodies, anti-gluten/tTG complex antibodies, anti-protamine sulfate antibodies, anti-protamine sulfate/tTG complex antibodies, anti-endomysial antibodies, anti-actin antibodies, anti-reticulin antibodies, anti-zonulin antibodies, anti-ATP synthase β chain antibodies, anti-enolase α antibodies, and anti jejunal antibodies; protein markers such as zonulin, motilin, interleukin, human leukocyte antigen (HLA), prolactin, soluble CD163; and combinations thereof. Any of a variety of classes (e.g., IgA, IgG, IgM, IgD, IgE) and subclasses of the antibody markers can be detected. In a preferred embodiment, a CD serology panel commercially available from Prometheus Laboratories Inc. (San Diego, Calif.) that is based on the detection of anti-gliadin antibodies, anti-endomysial antibodies, and anti-tTG antibodies is used to rule out CD.

Examples of genetic CD markers include, without limitation, class I major histocompatibility complex (MHC) genes such as HLA-A, HLA-B, and HLA-C; class II MHC genes such as HLA-D (e.g., HLA-DPA1, HLA-DPB1, HLA-DQA1, HLA-DQB1, HLA-DRA1, and HLA-DRB1); GM immunoglobulin allotypes (Zhong et al., *Nat. Genet.*, 14:329-333 (1996)); T-cell receptor genes such as TCRα, TCRβ, and TCRγ (Roschmann et al., *Gastroenterology*, 105:1790-1796 (1993)); a dipeptidyl peptidase IV gene (Clot et al., *J. Pediatr. Gastroenterol. Nutr.*, 30:464-466 (2000)); aminopeptidase N genes (Giordano et al., *Ann. Hum. Genet.*, 63 (Pt 3):207-215 (1999)); a cytotoxic T lymphocyte-associated 4 (CTLA4) gene (Djilali-Saiah et al., *Gut*, 43:187-189 (1998); Naluai et al., *Tissue Antigens*, 56:350-355 (2000); Popat et al., *Scand. J. Gastroenterol.*, 37:28-31 (2002); Mora et al., *Hum. Immunol.*, 64:297-301 (2003)); and combinations thereof. For example, polymorphisms in genetic markers such as those described in, e.g., Sollid et al., *Gastroenterol.*, 105:910-292 (1993) can be detected. In some embodiments, any of a combination of biochemical, serological, and genetic CD markers can be used to rule out CD. One skilled in the art will know of additional CD markers suitable for use in the present invention.

The determination of anti-gluten antibody levels in a sample is particularly useful in the present invention for ruling out CD. As used herein, the term "anti-gluten antibody" refers to an antibody that recognizes one or more of the glutamine- and proline-rich glutenin and prolamine proteins present in gluten or fragments thereof. In certain instances, an anti-gluten antibody can be directed to at least one glutenin or prolamine protein from wheat, barley, rye, millet, or oat, as well as deamidated counterparts or fragments thereof. Preferably, an anti-gluten antibody recognizes a prolamine protein such as a gliadin from wheat (e.g., A-gliadin, α-gliadin, γ-gliadin, Δ-gliadin, ε-gliadin, ω-gliadin), a secalin from rye, a hordein from barley, a panicin from millet, an avenin from oats, deamidated counterparts thereof, or fragments thereof.

In one embodiment, an anti-gluten antibody is directed to A-gliadin or a fragment thereof, e.g., a peptide containing amino acids 57 to 73 of A-gliadin or a deamidated counterpart thereof (Aleanzi et al., *Clin. Chem.*, 47:2023-2028 (2001)). In another embodiment, an anti-gluten antibody is directed to γ-gliadin or a fragment thereof, e.g., a peptide containing amino acids 138 to 153 of γ-gliadin or a deamidated counterpart thereof (Aleanzi et al., supra). In yet another embodiment, an anti-gluten antibody is directed to a secalin, a hordein, an avenin, or a fragment thereof, e.g., a peptide containing a sequence of secalin, hordein, avenin, or a deamidated counterpart thereof that is recognized by gluten-specific T-cell lines and/or clones from individuals with CD (Vader et al., *Gastroenterol.*, 125:1105-1113 (2003)).

In a preferred embodiment, an anti-gluten antibody is directed to an α-gliadin such as α2-gliadin or a fragment thereof, e.g., a peptide containing amino acids 57-89 of α2-gliadin or a deamidated counterpart thereof, known as the 33-mer peptide (Shan et al., *Science*, 297:2275-2279 (2002); PCT Patent Publication No. WO 03/068170). The 33-mer peptide, having the sequence LQLQPF-PQPQLPYPQPQLPYPQPQLPYPQPQPF (SEQ ID NO:1), is a multivalent peptide, containing multiple T cell or B cell epitopes, that is refractory to enzymatic digestion and is a substrate for tTG. A 33-mer peptide that has been deamidated by tTG at one or more glutamine residues acts as a potent stimulator of T cells.

Additional multivalent peptides that can be recognized by an anti-gluten antibody include, without limitation, peptides containing at least two T cell or B cell epitopes, preferably at least three epitopes, in which each epitope is either non-overlapping (i.e., sterically separate) or overlapping. In other words, a non-overlapping epitope refers to an epitope where the amino acids of a first epitope are not integral to the sequence of a second epitope and an overlapping epitope refers to an epitope where the amino acids of a first epitope are integral to the sequence of a second epitope. For peptides comprising non-overlapping epitopes, each distinct epitope is separated from another epitope by at least a peptide bond, and may be separated by one or more amino acids. As used herein, the term "epitope" refers to the portion of an antigen bound by an antibody or T cell receptor, which portion is sufficient for high affinity binding. In polypeptide antigens, generally a linear epitope for recognition will be at least about 7 amino acids in length, and may be 8 amino acids, 9 amino acids, 10 amino acids, or more.

Generally, the peptides comprise a sequence that may be represented by the formula:

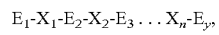

$$E_1\text{-}X_1\text{-}E_2\text{-}X_2\text{-}E_3 \ldots X_n\text{-}E_y,$$

where $E_1$, $E_2$ and $E_3$ are independently selected epitopes, which may be the same or different including, but not limited to, those having the amino acid sequence: PFPQPQLPY (SEQ ID NO:2), PQPQLPYPQ (SEQ ID NO:3), PQLPYPQPQ (SEQ ID NO:4), PYPQPQLPY (SEQ ID NO:5), PQPELPYPQ (SEQ ID NO:6), PFPQPELPY (SEQ ID NO:7), PQQSFPQQQ (SEQ ID NO:8), PFPQQPQQPFP (SEQ ID NO:9), PYPQPELPY (SEQ ID NO:10), deamidated counterparts thereof, and conservatively modified variants thereof, where $X_1$ and $X_2$ are independently selected spacers, which may be the same or different and comprise a peptide bond or one or more amino acids, where n is an integer of from 0-5, and y is an integer of from 0-5. If n=0 and y=0, then the peptide comprises the structure: $E_1\text{-}X_1\text{-}E_2\text{-}X_2\text{-}E_3$. For example, the 33-mer peptide (SEQ ID NO:1) has the following epitopic structure (where $X_1$ and $X_2$ are peptide bonds):

| LQLQ | PFPQPQLPY | PQPQLPYPQ | PQLPYPQPQ | PF |
|------|-----------|-----------|-----------|-----|
|      | $E_1$     | $E_2$     | $E_3$     |     |

Those of skill in the art will understand that additional epitopes (e.g., $E_4$, $E_5$, $E_6$, etc.), each separated by an additional peptide bond or one or more amino acids (e.g., $X_3$, $X_4$, $X_5$, etc.), are also within the scope of the present invention.

Alternatively, the peptides comprise at least one epitope that overlaps with at least one other epitope. As such, in the above formula, $E_1$ and $E_2$ and/or $E_2$ and $E_3$ are not separated by spacers such as $X_1$ and $X_2$, but instead contain at least one overlapping amino acid, preferably at least two or three amino acids, and more preferably at least four amino acids. Suitable overlapping epitopes include, but are not limited to, those having the amino acid sequence set forth in SEQ ID NOS:2-10, deamidated counterparts thereof, and conservatively modified variants thereof. As used herein, the term "conservatively modified variants" refers to functionally-preserved variants, which differ, usually in sequence, from the corresponding native or parent peptide but still retain the biological activity, i.e., epitopic specificity. Those of skill in the art will understand that peptides comprising a combination of non-overlapping and overlapping epitopes (e.g., $E_1$-$X_1$-$E_2$-$E_3$, $E_1$-$E_2$-$X_2$-$E_3$, etc.) are also within the scope of the present invention. For example, the 33-mer peptide (SEQ ID NO:1) has the following alternative epitopic structure (where $X_1$ is a peptide bond and $E_2$ and $E_3$ contain a four amino acid overlap, indicated in bold):

| LQLQ | PFPQPQLPY | PQPQLPYPQPQLPY | PQPQPF |
|------|-----------|--------------------|--------|
|      | $E_1$     | $E_2$-$E_3$        |        |

In certain instances, the peptides contain "flanking sequences," which as used herein refer to sequences comprising at least one amino acid at the amino terminus and/or carboxyl terminus of the peptide that is not an epitope. As such, the peptides can contain flanking sequences comprising one, two, three, four, or more amino acids at the amino terminus and/or at the carboxyl terminus, as long as the flanking sequences are not epitopes.

Other multivalent peptides that can be recognized by an anti-gluten antibody include, without limitation, QPQPFPPQLPYPQTQPFPPQQPYPQPQPQYPQPQ (SEQ ID NO:11) from α1- and α6-gliadin; QQQPFPQQPIPQQPQPYPQQPQPYPQQPFPPQQPF (SEQ ID NO:12) from B1 hordein; QPFPQPQQTFPQQPQLPFPQQPQQPFPQPQ (SEQ ID NO:13); PQQPQLPFPQQPQQPFPQPQQPQQPFPQSQQPQQPFPQPQQQFPQPQQPQQ SFPQQQQP (SEQ ID NO:14) from γ-gliadin; and QPFPQPQQPTPIQPQQPFPQRPQQPF PQPQ (SEQ ID NO:15). Similar to the 33-mer peptide, these oligopeptides are resistant to endo- and exo-proteolysis by gastric, pancreatic, and small intestinal enzymes, comprise multiple epitopes, and are recognized by tTG. See, e.g., Molberg et al., *Nat. Med.,* 4:713-717 (1998); Vader et al., *J. Exp. Med.,* 195:643-649 (2002); Sollid et al., *Ann. Rev. Immunol.,* 18:53-81 (2000); Vader et al., *Gastroenterol.,* 125:1105-1113 (2003); and Osman et al., *Clin. Exp. Immunol.,* 121, 248-254 (2003).

One skilled in art will understand that any of the above-described gluten antigens (e.g., proteins, peptides, or fragments thereof) can be used in an assay, e.g., an immunoassay, to detect or determine the level of one or more anti-gluten antibodies in a sample from an individual. Such gluten antigens can be synthesized, expressed, isolated, and/or purified according to any method known in the art.

The determination of anti-tissue transglutaminase (tTG) antibody levels in a sample is also particularly useful in the present invention for ruling out CD. As used herein, the term "anti-tissue transglutaminase (tTG) antibody" refers to an antibody that recognizes tissue transglutaminase (tTG) or a fragment thereof. Transglutaminases are a diverse family of $Ca^{2+}$-dependent enzymes that are ubiquitous and highly conserved across species. Of all the transglutaminases, tTG is the most widely distributed. Suitable substrates for tTG include, without limitation, any of the above-described gluten antigens. For example, when the 33-mer peptide is the substrate, tTG deamidates the peptide at one or more glutamine (Q) residues. One skilled in the art will understand that the tTG antigen or fragment thereof can be used in an assay, e.g., an immunoassay, to detect or determine the level of one or more anti-tTG antibodies in a sample from an individual. Such tTG antigens can be synthesized, expressed, isolated, and/or purified according to any method known in the art.

In another embodiment, anti-gluten/tTG complex antibody levels are determined in a sample for ruling out CD. As used herein, the term "anti-gluten/tTG complex antibody" refers to an antibody that recognizes a complex between tTG and gluten or a fragment thereof. Such a complex can be formed by means of a covalent or a non-covalent interaction between gluten and tTG. For example, gluten can be covalently attached to all or a portion of tTG or gluten can be covalently attached to tTG at a site of deamidation. Alternatively, gluten can interact non-covalently (e.g., ionic, van der Waal, hydrophobic, hydrogen bonding, etc.) with tTG. One skilled in art will understand that a complex between any of the above-described gluten and tTG antigens can be used in an assay, e.g., an immunoassay, to detect or determine the level of one or more anti-gluten/tTG complex antibodies in a sample from an individual.

In yet another embodiment, anti-protamine sulfate antibody and/or anti-protamine sulfate/tTG complex antibody levels are determined in a sample for ruling out CD. As used herein, the term "anti-protamine sulfate antibody" refers to an antibody that recognizes protamine sulfate or a fragment thereof. Similar to gluten, protamine sulfate proteins, peptides, or fragments thereof contain multiple glutamine (Q) residues and are substrates for tTG. One skilled in art will understand that the protamine sulfate antigen or fragment thereof can be used in an assay, e.g., an immunoassay, to detect or determine the level of one or more anti-protamine sulfate antibodies in a sample from an individual. Such protamine sulfate antigens can be synthesized, expressed, isolated, and/or purified according to any method known in the art. Likewise, the term "anti-protamine sulfate/tTG complex antibody" refers to an antibody that recognizes a complex between protamine sulfate and tTG. Such a complex can be formed by means of a covalent or a non-covalent interaction between protamine sulfate and tTG. For example, protamine sulfate can be covalently attached to all or a portion of tTG or protamine sulfate can be covalently attached to tTG at a site of deamidation. Alternatively, protamine sulfate can interact non-covalently with tTG. One skilled in art will understand that a complex between protamine sulfate and tTG antigens can be used in an assay, e.g., an immunoassay, to detect or determine the level of one or more anti-protamine sulfate/tTG complex antibodies in a sample from an individual.

In still yet another embodiment, anti-endomysial antibody levels are determined in a sample for ruling out CD. As used herein, the term "anti-endomysial antibody" refers to an antibody that recognizes the tTG component of smooth muscle endomysium or a fragment thereof. One skilled in art will understand that the endomysial antigen or fragment thereof can be used in an assay, e.g., an immunoassay, to detect or determine the level of one or more anti-endomysial antibodies in a sample from an individual. Such endomysial antigens can be synthesized, expressed, isolated, and/or purified according to any method known in the art.

In a further embodiment, anti-actin antibody levels are determined in a sample for ruling out CD. As used herein, the term "anti-actin antibody" refers to an antibody that recognizes actin or a fragment thereof. One skilled in art will understand that the actin antigen or fragment thereof can be used in an assay, e.g., an immunoassay, to detect or determine the level of one or more anti-actin antibodies in a sample from an individual. Such actin antigens can be synthesized, expressed, isolated, and/or purified according to any method known in the art.

In an additional embodiment, anti-reticulin antibody levels are determined in a sample for ruling out CD. As used herein, the term "anti-reticulin antibody" refers to an antibody that recognizes a component of the reticulin network or a fragment thereof. One skilled in art will understand that the reticulin antigen or fragment thereof can be used in an assay, e.g., an immunoassay, to detect or determine the level of one or more anti-reticulin antibodies in a sample from an individual. Such reticulin antigens can be synthesized, expressed, isolated, and/or purified according to any method known in the art.

In another embodiment, anti-zonulin antibody levels are determined in a sample for ruling out CD. As used herein, the term "anti-zonulin antibody" refers to an antibody that recognizes zonulin or a fragment thereof. One skilled in art will understand that the zonulin antigen or fragment thereof can be used in an assay, e.g., an immunoassay, to detect or determine the level of one or more anti-zonulin antibodies in a sample from an individual. Such zonulin antigens can be synthesized, expressed, isolated, and/or purified according to any method known in the art.

In yet another embodiment, anti-ATP synthase β chain antibody levels are determined in a sample for ruling out CD. As used herein, the term "anti-ATP synthase β chain antibody" refers to an antibody that recognizes the β chain of ATP synthase or a fragment thereof. One skilled in art will understand that the ATP synthase chain β antigen or fragment thereof can be used in an assay, e.g., an immunoassay, to detect or determine the level of one or more anti-ATP synthase β chain antibodies in a sample from an individual. Such ATP synthase β chain antigens can be synthesized, expressed, isolated, and/or purified according to any method known in the art.

In still yet another embodiment, anti-enolase α antibody levels are determined in a sample for ruling out CD. As used herein, the term "anti-enolase α antibody" refers to an antibody that recognizes enolase α or a fragment thereof. One skilled in art will understand that the enolase α antigen or fragment thereof can be used in an assay, e.g., an immunoassay, to detect or determine the level of one or more anti-enolase α antibodies in a sample from an individual. Such enolase α antigens can be synthesized, expressed, isolated, and/or purified according to any method known in the art.

In a further embodiment, anti jejunal antibody levels are determined in a sample for ruling out CD. As used herein, the term "anti jejunal antibody" refers to an antibody that recognizes a jejuna' antigen or a fragment thereof. One skilled in art will understand that the jejunal antigen or fragment thereof ca-n be used in an assay, e.g., an immunoassay, to detect or determine the level of one or more anti jejunal antibodies in a sample from an individual. Such jejunal antigens can be synthesized, expressed, isolated, and/or purified according to any method known in the art.

In an additional embodiment, zonulin levels are determined in a sample for ruling out CD. As used herein, the term "zonulin" refers to a protein that is immunologically and functionally related to zonula occludens toxin (ZOT) and acts as a modulator of tight junctions. One skilled in art will understand that the presence or level of zonulin can be determined with an assay that uses a zonulin-binding molecule such as an anti-zonulin antibody, an anti-ZOT antibody, an extracellular zonulin-binding protein (e.g., zonulin receptor, ZOT receptor), fragments thereof, or the like.

In another embodiment, motilin levels are determined in a sample for ruling out CD. As used herein, the term "motilin" refers to a peptide that is secreted by endocrinocytes in the mucosa of the proximal small intestine. One skilled in art will understand that the presence or level of motilin can be determined with an assay that uses a motilin-binding molecule such as an anti-motilin antibody, an extracellular motilin-binding protein (e.g., motilin receptor), fragments thereof, or the like.

In yet another embodiment, interleukin levels are determined in a sample for ruling out CD. As used herein, the term "interleukin" refers to any of a variety of cytokines secreted by immune cells that regulate a range of immune system functions. One skilled in art will understand that the presence or level of one or more interleukins including, without limitation, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, etc. can be determined with an assay that uses an interleukin-binding molecule such as an anti-interleukin antibody, an extracellular interleukin-binding protein (e.g., interleukin receptor), fragments thereof, or the like. Preferably, the interleukin is IL-18.

In still yet another embodiment, human leukocyte antigen (HLA) levels are determined in a sample for ruling out CD. As used herein, the term "human leukocyte antigen (HLA)" refers to any of a variety of proteins at the cell surface that present antigens to immune cells such as T cells. One skilled in art will understand that the presence or level of one or more HLAs including, without limitation, HLA-A, HLA-B, HLA-C, HLA-DPA1, HLA-DPB1, HLA-DQA1, HLA-DQB1, HLA-DRA1, and HLA-DRB1 can be determined with an assay that uses an HLA-binding molecule such as an anti-HLA antibody, a cytosolic HLA-binding protein, an extracellular HLA-binding protein, fragments thereof, or the like.

In a further embodiment, prolactin levels are determined in a sample for ruling out CD. As used herein, the term "prolactin" refers to a single-chain protein hormone closely related to growth hormone that is secreted by the anterior pituitary and various immune cells. One skilled in art will understand that the presence or level of prolactin can be determined with an assay that uses a prolactin-binding molecule such as an anti-prolactin antibody, an extracellular prolactin-binding protein (e.g., prolactin receptor), fragments thereof, or the like.

In an additional embodiment, soluble CD163 levels are determined in a sample for ruling out CD. As used herein, the term "soluble CD163" refers to the soluble form of CD163, a protein that belongs to the scavenger receptor family and is expressed selectively on most macrophages and on a subset of monocytes. In certain instances, the activation of macrophages induces the shedding of CD163 from the cell surface to form soluble CD163. One skilled in art will understand that the presence or level of soluble CD163 can be determined with an assay that uses a CD163-binding molecule such as an anti-CD163 antibody, an extracellular CD163-binding protein (e.g., CD163 ligand), fragments thereof, or the like.

VII. Colorectal Cancer

In another embodiment, the present invention rules out colorectal cancer, based upon a physical exam, medical history, risk factors, and/or other diagnostic tests. These diagnostic tests include, for example, X-rays of the large intestine, which can reveal polyps or other changes. A sigmoidoscopy can reveal abnormal tissue for examination under a microscope. Further, a biopsy for examination under a microscope by a pathologist can be used to make a diagnosis and to rule out cancer.

VIII. Assays

Any of a variety of assays, techniques, and kits known in the art can be used to determine the presence or level of one or more markers in a sample to classify whether the sample is associated with IBS.

The present invention relies, in part, on determining the presence or level of at least one marker in a sample obtained from an individual. As used herein, the term "determining the presence of at least one marker" refers to determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" refers to determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

As used herein, the term "antibody" refers to a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop and Davis, *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego: Academic Press, Inc. (1996)).

A variety of immunoassay techniques, including competitive and non-competitive immunoassays, can be used to determine the presence or level of one or more markers in a sample (see, e.g., Self and Cook, *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis,* 18:2184-93 (1997); Bao, *J. Chromatogr. B. Biomed. Sci.,* 699:463-80 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the biomarker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more IBD markers in a sample. A fixed neutrophil ELISA, for example, is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein or a fragment thereof is useful for determining whether a sample is positive for anti-flagellin antibodies, or for determining anti-flagellin antibody levels in a sample. In addition, the immunoassays described above are particularly useful for determining the presence or level of one or more IBS or CD markers in a sample.

Immunoassays such as sandwich ELISAs are also particularly useful for determining the presence or level of C-reactive protein (CRP) or lactoferrin or calprotectin in a sample. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. A lactoferrin ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. U.S. Patent Publication No. 20040137536 describes an ELISA assay for determining the presence of elevated lactoferrin levels in a stool sample. Likewise, U.S. Patent Publication No. 20040033537 describes an ELISA assay for determining the concentration of endogenous lactoferrin in a stool, mucus, or bile sample.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684 all incorporated herein by reference.

Calprotectin is a calcium and zinc-binding protein found in all cells, tissues, and fluids in the body. Calprotectin is a major protein in neutrophilic granulocytes and macrophages and accounts for as much as 60% of the total protein in the cytosol fraction in these cells. It is therefore a surrogate marker of neutrophile turnover. Its concentration in stool correlates with the intensity of neutrophile infiltration of the intestinal mucosa and with the severity of inflammation. Calprotectin can be measured with an enzyme linked immunosorbent assay (ELISA) using small (50-100 mg) feces samples (see, for example, Johne B et al., *Scand J Gastroenterol.* 2001 March; 36(3):291-6.).

Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449-430) and can be performed using a Behring Nephelometer Analyzer (Fink et al., *J. Clin. Chem. Clin. Biol. Chem.,* 27:261-276 (1989)).

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample.

Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting also can be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., Nature Biotech., 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful information to rule out diseases and disorders associated with IBS-like symptoms and/or to rule in IBS.

A panel consisting of one or more of the markers described above may be constructed to provide relevant information related to the "rule-out/rule-in" approach of the present invention for classifying a sample as being associated with IBS. Such a panel may be constructed using 1, 2, 3, 4, 5, 6, 7, 8, 9, 10, 15, 20, or more or individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

IX. Statistical Algorithms

The present invention provides methods and systems for classifying whether a sample is associated with IBS using a first statistical algorithm to classify the sample as a non-IBD sample or as an IBD sample (i.e., IBD rule-out step) followed by a second statistical algorithm to classify the non-IBD sample as an IBS sample or as a non-IBS sample (i.e., IBS rule-in step). Preferably, both the first and second statistical algorithms independently comprise one or more learning statistical classifier systems. As described herein, a combination of learning statistical classifier systems advantageously provides improved sensitivity, specificity, negative predictive value, positive predictive value, and/or overall accuracy for ruling out IBD or ruling in IBS.

The term "statistical algorithm" or "statistical process" refers to any of a variety of statistical analyses used to determine relationships between variables. In the present invention, the variables are the presence or level of at least one marker of interest. Any number of markers can be analyzed using a statistical algorithm described herein. For example, the presence or levels of 1, 2, 3, 4, 5, 6, 7, 8, 9, 10, 15, 20, 25, 30, 35, 40, 50, or more markers can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

Preferably, the statistical algorithms of the present invention comprise one or more learning statistical classifier systems. As used herein, the term "learning statistical classifier system" refers to a machine learning algorithmic technique capable of adapting to complex data sets (e.g., panel of markers of interest) and making decisions based upon such data sets.

In preferred embodiments of the present invention, one or more learning statistical classifier systems are used, e.g., 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (CART), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the CART software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

In one embodiment, the first statistical algorithm is a combination of learning statistical classifier systems that provides improved sensitivity for ruling out IBD (i.e., classifying a sample as a non-IBD sample). In another embodiment, the second statistical algorithm is a combination of learning statistical classifier systems that provides improved sensitivity for ruling in IBS (i.e., classifying the non-IBD sample as an ms sample). As used herein, the term "sensitivity" refers to the probability that a statistical algorithm of the present invention gives a positive result when the sample is positive, e.g., having IBD or IBS. Sensitivity is calculated as the number of true positive results divided by the sum of the true positives and false negatives. Sensitivity essentially is a measure of how well a statistical algorithm of the present invention correctly identifies those with IBD or IBS from those without the disease. The marker values or learning statistical classifier models (e.g., support vector machine or neural network models) can be selected such that the sensitivity of classifying IBD in a sample or classifying IBS in a non-IBD sample is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In one preferred embodiment, the sensitivity of classifying IBD in a sample is at least about 85% when a tandem arrangement of random forest and neural network learning statistical classifier systems is used. In another preferred embodiment, the sensitivity of classifying IBS in a non-IBD sample is at least about 80% when a tandem arrangement of random forest and support vector machine learning statistical classifier systems is used.

In another embodiment, the first statistical algorithm is a combination of learning statistical classifier systems that provides improved specificity for ruling out IBD. In yet another embodiment, the second statistical algorithm is a combination of learning statistical classifier systems that provides improved specificity for ruling in IBS. As used herein, the term "specificity" refers to the probability that a statistical algorithm of the present invention gives a negative result when the sample is not positive, e.g., not having IBD or IBS. Specificity is calculated as the number of true negative results divided by the sum of the true negatives and false positives. Specificity essentially is a measure of how well a statistical algorithm of the present invention excludes those who do not have IBD or IBS from those who have the disease. The marker values or learning statistical classifier models can be selected such that the specificity of classifying IBD in a sample or classifying IBS in a non-IBD sample is at least about 70%, for example, at least about 75%, 80%, 85%, 86%, 87%, 88%, 89%, 90%, 91%, 92%, 93%, 94%, 95%, 96%, 97%, 98%, or 99%. In one preferred embodiment, the specificity of classifying IBD in a sample is at least about 75% when a tandem arrangement of random forest and neural network learning statistical classifier systems is used. In another preferred embodiment, the specificity of classifying IBS in a non-IBD sample is at least about 85% when a tandem arrangement of random forest and support vector machine learning statistical classifier systems is used.

In yet another embodiment, the first statistical algorithm is a combination of learning statistical classifier systems that provides improved negative predictive value for ruling out IBD. In still yet another embodiment, the second statistical algorithm is a combination of learning statistical classifier systems that provides improved negative predictive value for ruling in IBS. As used herein, the term "negative predictive value" or "NPV" refers to the probability that an individual classified as not having IBD or IBS actually does not have the disease. Negative predictive value can be calculated as the number of true negatives divided by the sum of the true negatives and false negatives. Negative predictive value is determined by the characteristics of the statistical algorithm as well as the prevalence of the disease in the population analyzed. The marker values or learning statistical classifier models can be selected such that the negative predictive value in a population having a disease prevalence is at least about 70% and can be, for example, at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In one preferred embodiment, the negative predictive value of classifying IBD in a sample is at least about 97% when a tandem arrangement of random forest and neural network learning statistical classifier systems is used. In another preferred embodiment, the negative predictive value of classifying IBS in a non-IBD sample is at least about 90% when a tandem arrangement of random forest and support vector machine learning statistical classifier systems is used.

In still yet another embodiment, the first statistical algorithm is a combination of learning statistical classifier systems that provides improved positive predictive value for ruling out IBD. In a further embodiment, the second statistical algorithm is a combination of learning statistical classifier systems that provides improved positive predictive value for ruling in IBS. As used herein, the term "positive predictive value" or "PPV" refers to the probability that an individual classified as having IBD or IBS actually has the disease. Positive predictive value can be calculated as the number of true positives divided by the sum of the true positives and false positives. Positive predictive value is determined by the characteristics of the statistical algorithm as well as the prevalence of the disease in the population analyzed. The marker values or learning statistical classifier models can be selected such that the positive predictive value in a population having a disease prevalence is at least about 25% and can be, for example, at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%. In one preferred embodiment, the positive predictive value of classifying IBD in a sample is at least about 35% when a tandem arrangement of random forest and neural network learning statistical classifier systems is used. In another preferred embodiment, the positive predictive value of classifying IBS in a non-IBD sample is at least about 70% when a tandem arrangement of random forest and support vector machine learning statistical classifier systems is used.

Predictive values, including negative and positive predictive values, are influenced by the prevalence of the disease in the population analyzed. In the statistical algorithms of the present invention, the marker values or learning statistical classifier models can be selected to produce a desired clinical parameter for a clinical population with a particular IBD or IBS prevalence. For example, marker values or learning statistical classifier models can be selected for an IBD or IBS prevalence of at least about 1%, 5%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

In a further embodiment, the first statistical algorithm is a combination of learning statistical classifier systems that provides improved overall accuracy for ruling out IBD. In another embodiment, the second statistical algorithm is a combination of learning statistical classifier systems that provides improved overall accuracy for ruling in IBS. As used herein, the term "overall accuracy" or "overall agreement" refers to the accuracy with which a statistical algorithm of the present invention classifies a disease state. Overall accuracy is calculated as the sum of the true positives and true negatives divided by the total number of sample results and is affected by the prevalence of the disease in the population analyzed. For example, the marker values or learning statistical classifier models can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 95%, 96%, 97%, 98%, or 99%. In one preferred embodiment, the overall accuracy of classifying IBD in a sample is at least about 90% when a tandem arrangement of random forest and neural network learning statistical classifier systems is used. In another preferred embodiment, the overall accuracy of classifying IBS in a non-MD sample is at least about 80% when a tandem arrangement of random forest and support vector machine learning statistical classifier systems is used.

The learning statistical classifier systems described herein can be trained and tested using a cohort of samples (e.g., serological samples) from healthy individuals, IBS patients, and/or IBD patients. For example, samples from patients diagnosed by a physician, and preferably by a gastroenterologist as having IBD using a biopsy, colonoscopy, or an immunoassay as described in, e.g., U.S. Pat. No. 6,218,129 (incorporated herein by reference), are suitable for use in training and testing the learning statistical classifier systems of the present invention. Samples from patients diagnosed with IBD can also be stratified into Crohn's disease or ulcerative colitis using an immunoassay as described in, e.g., U.S. Pat. Nos. 5,750,355 and 5,830,675 (both incorporated herein by reference). Samples from patients diagnosed with IBS using a published criteria such as the Maiming, Rome I, or Rome II diagnostic criteria are suitable for use in training and testing the learning statistical classifier systems of the present invention. The Rome II diagnostic criteria, which diagnoses IBS on the basis of at least 12 weeks (which need not be consecutive) in the preceding 12 months of abdominal discomfort or pain that has two out of three of these features: (1) relieved with defecation; and/or (2) onset associated with a change in frequency of stool; and/or (3) onset associated with a change in form (appearance) of stool, is particularly useful for identifying IBS samples that can be used in the training and testing sets for developing the learning statistical classifier systems of the present invention. Samples from healthy individuals can include those that were not identified as IBD and/or IBS samples. One skilled in the art will know of additional techniques and diagnostic criteria for obtaining a cohort of patient samples that can be used in training and testing the learning statistical classifier systems of the present invention.

X. Disease Classification System

Figure 2:
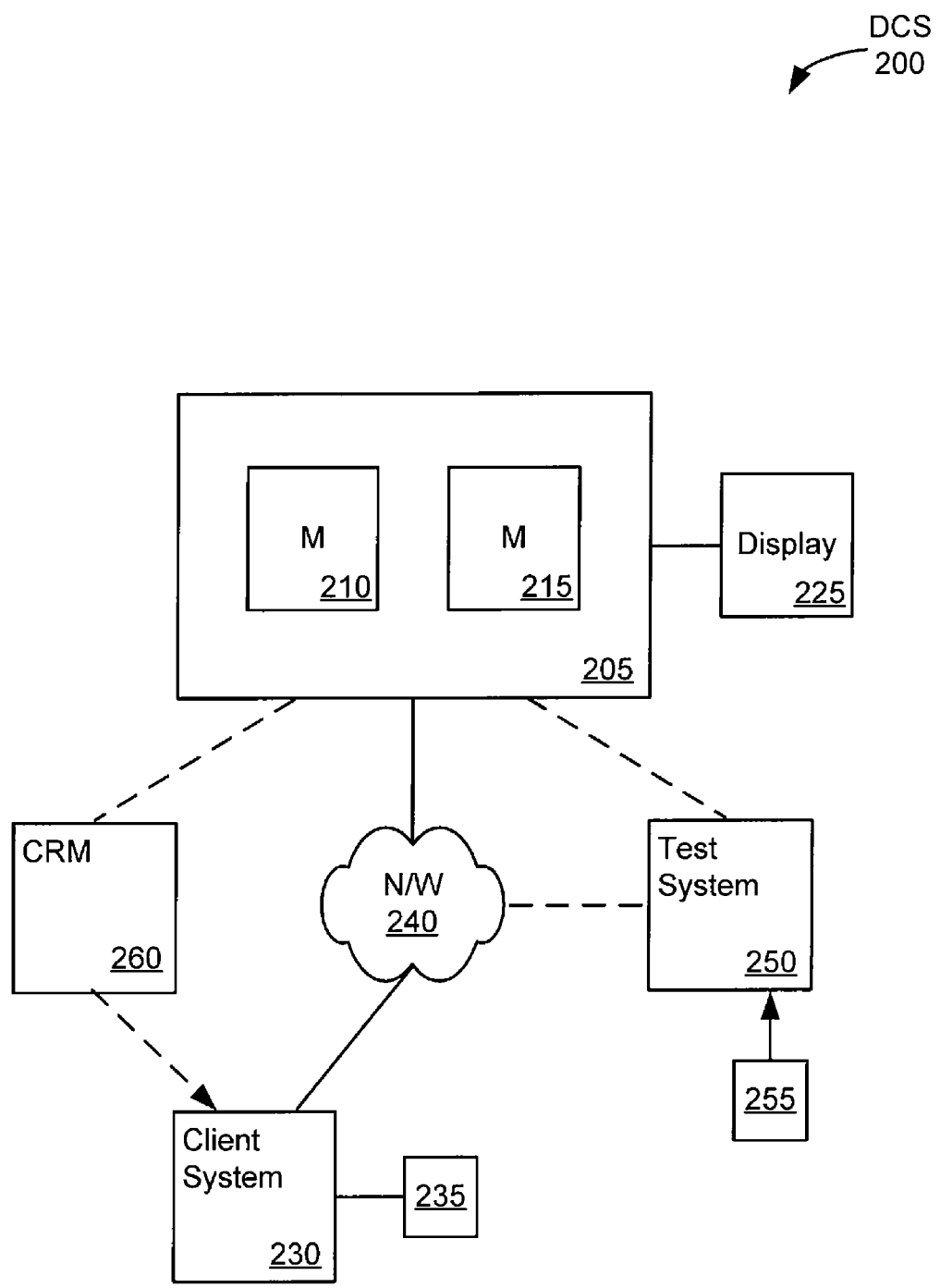
FIG. 2 illustrates a disease classification system (DCS) according to one embodiment of the present invention.

FIG. 2 illustrates a disease classification system (DCS) (200) according to one embodiment of the present invention. As shown therein, a DCS includes a DCS intelligence module (205), such as a computer, having a processor (215) and memory module (210). The intelligence module also includes communication modules (not shown) for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module (225), such as a monitor or printer. In one aspect, the intelligence module receives data such as patient test results from a data acquisition module such as a test system (250), either through a direct connection or over a network (240). For example, the test system may be configured to run multianalyte tests on one or more patient samples (255) and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems (230) over the network as is well known. For example, a requesting physician or healthcare provider may obtain and view a report from the intelligence module, which may be resident in a laboratory or hospital, using a client system (230).

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system shown in FIG. 2 may include conventional, well-known elements that need not be explained in detail here. For example, the intelligence module could be implemented as a desktop personal computer, workstation, mainframe, laptop, etc. Each client system could include a desktop personal computer, workstation, laptop, PDA, cell phone, or any WAP-enabled device or any other computing device capable of interfacing directly or indirectly to the Internet or other network connection. A client system typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of the client system to access, process, and view information and pages available to it from the intelligence module over the network. Each client system also typically includes one or more user interface devices, such as a keyboard, a mouse, touch screen, pen or the like, for interacting with a graphical user interface (GUI) provided by the browser on a display (e.g., monitor screen, LCD display, etc.) (235) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel Pentium processor or the like. Similarly, the intelligence module and all of its components might be operator configurable using application(s) including computer code run using a central processing unit (215) such as an Intel Pentium processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium (260) capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C#, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/I P, HTTP, HTTPS, Ethernet, etc.) as are well known.

According to one embodiment, the intelligence module implements a disease classification process for analyzing patient test results to determine whether a patient sample is associated with irritable bowel syndrome (IBS). The data may be stored in one or more data tables or other logical data structures in memory (210) or in a separate storage or database system coupled with the intelligence module. Initially, a first statistical process is applied to a data set including test data for the patient sample. In one aspect, for example, the test data might include data indicating the presence or level of at least one inflammatory bowel disease (IBD) marker in the patient sample. The first statistical process produces a first statistically derived decision classifying the patient sample as an inflammatory bowel disease (IBD) sample or as a non-IBD sample based upon the presence or level of the at least one IBD marker. If the patient sample is classified as a non-IBD sample, a second statistical process is applied to the data set to produce a second statistically derived decision classifying the non-IBD sample as an IBS sample or a non-IBS sample based upon the presence or level of the at least one IBD marker. The first and/or the second statistically derived decision may be displayed on a display device associated with or coupled to the intelligence module, or the decision(s) may be provided to and displayed at a separate system, e.g., a client system (230). The displayed results allow a physician to make a reasoned diagnosis.

XI. Therapy and Therapeutic Monitoring

Once a sample from an individual has been classified as an IBS sample, the methods of the present invention can further comprise administering to the individual a therapeutically effective amount of a drug useful for treating one or more symptoms associated with IBS (i.e., an IBS drug). For therapeutic applications, the IBS drug can be administered alone or co-administered in combination with one or more additional IBS drugs and/or one or more drugs that reduce the side-effects associated with the IBS drug.

IBS drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an IBS drug is administered at the same time, just prior to, or just after the administration of a second drug (e.g., another IBS drug, a drug useful for reducing the side-effects of the IBS drug, etc.).

A therapeutically effective amount of an IBS drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an IBS drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBS drug.

Methods for preparing such dosage forms are known to those skilled in the art (see, e.g., *Remington's Pharmaceutical Sciences*, 18*th* ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *Remington's Pharmaceutical Sciences*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBS drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBS drug can also be formulated into a suppository disposed, for example, in a polyethylene glycol (PEG) carrier.

Liquid dosage forms can be prepared by dissolving or dispersing an IBS drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBS drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBS drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBS, an IBS drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBS symptoms, and the IBS drug being employed. For example, dosages can be empirically determined considering the severity of IBS symptoms in an individual classified as having IBS according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBS drug in an individual. Determination of the proper dosage for a particular situation is within the skill of the practitioner. Generally, treatment is initiated with smaller dosages which are less than the optimum dose of the IBS drug. Thereafter, the dosage is increased by small increments until the optimum effect under circumstances is reached. For convenience, the total daily dosage may be divided and administered in portions during the day, if desired.

As used herein, the term "IBS drug" includes all pharmaceutically acceptable forms of a drug that is useful for treating one or more symptoms associated with IBS. For example, the IBS drug can be in a racemic or isomeric mixture, a solid complex bound to an ion exchange resin, or the like. In addition, the IBS drug can be in a solvated form. The term "IBS drug" is also intended to include all pharmaceutically acceptable salts, derivatives, and analogs of the IBS drug being described, as well as combinations thereof. For example, the pharmaceutically acceptable salts of an IBS drug include, without limitation, the tartrate, succinate, tartarate, bitartrate, dihydrochloride, salicylate, hemisuccinate, citrate, maleate, hydrochloride, carbamate, sulfate, nitrate, and benzoate salt forms thereof, as well as combinations thereof and the like. Any form of an IBS drug is suitable for use in the methods of the present invention, e.g., a pharmaceutically acceptable salt of an IBS drug, a free base of an IBS drug, or a mixture thereof.

Suitable drugs that are useful for treating one or more symptoms associated with IBS include, but are not limited to, serotonergic agents, antidepressants, chloride channel activators, guanylate cyclase agonists, antibiotics, opioids, neurokinin antagonists, antispasmodic or anticholinergic agents, belladonna alkaloids, barbiturates, free bases thereof, pharmaceutically acceptable salts thereof, derivatives thereof, analogs thereof, and combinations thereof. Other IBS drugs include bulking agents, dopamine antagonists, carminatives, tranquilizers, phenyloin, timolol, and diltiazem.

Serotonergic agents are useful for the treatment of IBS symptoms such as constipation, diarrhea, and/or alternating constipation and diarrhea. Non-limiting examples of serotonergic agents are described in Cash et al., *Aliment. Pharmacol. Ther.*, 22:1047-1060 (2005), and include 5-$HT_3$ receptor agonists (e.g., MKC-733, etc.), 5-$HT_4$ receptor agonists (e.g., tegaserod, prucalopride, etc.), 5-$HT_3$ receptor antagonists (e.g., alosetron, cilansetron, ondansetron, granisetron, dolasetron, ramosetron, palonosetron, etc.), mixed 5-$HT_3$ receptor antagonists/5-$HT_4$ receptor agonists (e.g., cisapride, mosapride, renzapride, etc.), free bases thereof, pharmaceutically acceptable salts thereof, derivatives thereof, analogs thereof, and combinations thereof. Additionally, amino acids like glutamine and glutamic acid which regulate intestinal permeability by affecting neuronal or glial cell signaling can be administered to treat patients with IBS.

Antidepressants such as selective serotonin reuptake inhibitor (SSRI) or tricyclic antidepressants are particularly useful for the treatment of IBS symptoms such as abdominal pain, constipation, and/or diarrhea. Non-limiting examples of SSRI antidepressants include citalopram, fluvoxamine, paroxetine, fluoxetine, sertraline, free bases thereof, pharmaceutically acceptable salts thereof, derivatives thereof, analogs thereof, and combinations thereof. Examples of tricyclic antidepressants include, but are not limited to, desipramine, nortriptyline, protriptyline, amitriptyline, clomipramine, doxepin, imipramine, trimipramine, maprotiline, amoxapine, clomipramine, free bases thereof, pharmaceutically acceptable salts thereof, derivatives thereof, analogs thereof, and combinations thereof.

Chloride channel activators are also useful for the treatment of IBS symptoms such as constipation. A non-limiting example of a chloride channel activator is lubiprostone, a free base thereof, a pharmaceutically acceptable salt thereof, a derivative thereof, or an analog thereof. In addition, guanylate cyclase agonists such as MD-1100 are useful for the treatment of constipation associated with IBS (see, e.g., Bryant et al., *Gastroenterol.*, 128:A-257 (2005)). Antibiotics such as neomycin can also be suitable for use in treating constipation associated with IBS (see, e.g., Park et al., *Gastroenterol.*, 128:A-258 (2005)). Non-absorbable antibiotics like Rifaximin are suitable to treat small bowel bacterial overgrowth in IBS (see, e.g., Shanara et al., *Am. J. Gastroenterol.*, 101-326 (2006)).

Opioids such as kappa opioids (e.g., asimadoline) may be useful for treating pain associated with IBS. Neurokinin antagonists such as talnetant may be useful for treating IBS symptoms such as oversensitivity of the muscles in the colon. Antispasmodic or anticholinergic agents such as dicyclomine may be useful for treating IBS symptoms such as spasms in the muscles of the gut and bladder. Other antispasmodic or anticholinergic agents such as belladonna alkaloids (e.g., atropine, scopolamine, hyoscyamine, etc.) can be used in combination with barbiturates such as phenobarbital to reduce bowel spasms associated with IBS. One skilled in the art will know of additional IBD drugs currently in use or in development that are suitable for treating one or more symptoms associated with IBS.

An individual can also be monitored at periodic time intervals to assess the efficacy of a certain therapeutic regimen once a sample from the individual has been classified as an IBS sample. For example, the levels of certain markers change based on the therapeutic effect of a treatment such as a drug. The patient is monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

XII. Examples

The following examples are offered to illustrate, but not to limit, the claimed invention.

Example 1

Determination of ANCA Levels

This example illustrates an analysis of ANCA levels in a sample using an enzyme-linked immunosorbent assay (ELISA).

A fixed neutrophil ELISA was used to detect ANCA as described in Saxon et al., *J. Allergy Clin. Immunol.*, 86:202-210 (1990). Briefly, microtiter plates were coated with about $2.5 \times 10^5$ neutrophils per well from peripheral human blood purified by Ficoll-hypaque centrifugation and treated with 100% methanol for 10 minutes to fix the cells. Cells were incubated with 0.25% bovine serum albumin (BSA) in phosphate-buffered saline to block nonspecific antibody binding for 60 minutes at room temperature in a humidified chamber. Next, control and coded sera were added at a 1:100 dilution to the bovine serum/phosphate-buffered saline blocking buffer and incubated for 60 minutes at room temperature in a humidified chamber. Alkaline phosphatase-conjugated goat F(ab')$_2$ anti-human immunoglobulin G antibody (γ-chain specific; Jackson Immunoresearch Labs, Inc.; West Grove, Pa.) was added at a 1:1000 dilution to label neutrophil-bound antibody and incubated for 60 minutes at room temperature. A solution of p-nitrophenol phosphate substrate was added, and color development was allowed to proceed until absorbance at 405 nm in the positive control wells was 0.8-1.0 optical density units greater than the absorbance in blank wells. ANCA positive reactivity was defined as reactivity greater than two standard deviations above the mean reactivity obtained with control (normal) sera analyzed at the same time as the test samples.

Example 2

Determination of ASCA Levels

This example illustrates the preparation of yeast cell well mannan and an analysis of ASCA levels in a sample using ELISA.

Yeast cell wall mannan was prepared as described in Faille et al., *Eur. J. Clin. Microbiol. Infect. Dis.*, 11:438-446 (1992) and in Kocourek et al., *J. Bacteria*, 100:1175-1181 (1969). Briefly, a lyophilized pellet of yeast *Saccharomyces uvarum* was obtained from the American Type Culture Collection (#38926). Yeast were reconstituted in 10 ml 2×YT medium, prepared according to Sambrook et al., In "Molecular Cloning," Cold Spring Harbor Laboratory Press (1989). *S. uvarum* were grown for two to three days at 30° C. The terminal *S. uvarum* culture was inoculated on a 2×YT agar plate and subsequently grown for two to three days at 30° C. A single colony was used to inoculate 500 ml 2×YT media, and grown for two to three days at 30° C. Fermentation media (pH 4.5) was prepared by adding 20 g glucose, 2 g bacto-yeast extract, 0.25 g MgSO$_4$, and 2.0 ml 28% H$_3$PO$_4$ per liter of distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 g/l sodium citrate; pH 7.0±0.1) to each 100 g of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant was retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6-8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded, then the wash procedure was repeated until the supernatant was colorless, approximately two to three times. The precipitate was collected on a scintered glass funnel, washed with methanol, and air dried overnight. On some occasions, the precipitate was collected by centrifugation at 5000 rpm for 10 minutes before washing with methanol and air drying overnight. The dried mannan powder was dissolved in distilled water to a concentration of approximately 2 g/ml.

A *S. uvarum* mannan ELISA was used to detect ASCA. *S. uvarum* mannan ELISA plates were saturated with antigen as follows. Purified *S. uvarum* mannan prepared as described above was diluted to a concentration of 100 µg/ml with phosphate buffered saline/0.2% sodium azide. Using a multichannel pipettor, 100 µl of 100 µg/ml *S. uvarum* mannan was added per well of a Costar 96-well hi-binding plate (catalog no. 3590; Costar Corp., Cambridge, Mass.). The antigen was allowed to coat the plate at 4° C. for a minimum of 12 hours. Each lot of plates was compared to a previous lot before use. Plates were stored at 2-8° C. for up to one month.

Patient sera were analyzed in duplicate for ASCA-IgA or ASCA-IgG reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:80 for analysis of ASCA-IgA and 1:800 for analysis of ASCA-IgG and incubated for 1 hour at room temperature. Wells were washed three times with PBS/0.05% Tween-20. Then, a 1:1000 dilution of alkaline phosphatase-conjugated goat anti-human IgA (Jackson Immunoresearch; West Grove, Pa.) or a 1:1000 dilution of alkaline phosphatase-conjugated goat anti-human IgG F(ab')$_2$ (Pierce; Rockford, Ill.) was added, and the microtiter plates were incubated for 1 hour at room temperature. A solution of p-nitrophenol phosphate in diethanolamine substrate buffer was added, and color development was allowed to proceed for 10 minutes.

Absorbance at 405 nm was analyzed using an automated EMAX plate reader (Molecular Devices; Sunnyvale, Calif.). ASCA-IgA or ASCA-IgG positive reactivity was defined as reactivity greater than two standard deviations above the mean reactivity obtained with control (normal) sera analyzed at the same time as the test samples.

Example 3

Determination of Anti-I2 Antibody Levels

This example illustrates the preparation of recombinant I2 protein and an analysis of anti-I2 antibody levels in a sample using ELISA or a histological assay.

The full-length I2-encoding nucleic acid sequence was cloned into the GST expression vector pGEX. After expression in *E. coli*, the protein was purified on a GST column. The purified protein was shown to be of the expected molecular weight by silver staining, and had anti-GST reactivity upon Western blot analysis.

Human IgA and IgG antibodies that bind the GST-I2 fusion polypeptide were detected by direct ELISA assays essentially as follows. Plates (Immulon 3; DYNEX Technologies; Chantilly, Va.) were coated overnight at 4° C. with 100 µl/well GST-I2 fusion polypeptide (5 µg/ml in borate buffered saline, pH 8.5). After three washes in 0.05% Tween 20 in phosphate buffered saline (PBS), the plates were blocked with 150 µl/well of 0.5% bovine serum albumin in PBS, pH 7.4 (BSA-PBS) for 30 minutes at room temperature. The blocking solution was then replaced with 100 µl/well of test serum or normal control serum, diluted 1:100. The plates were then incubated for 2 hours at room temperature and washed as before. Alkaline phosphatase-conjugated secondary antibody (goat anti-human IgA (α-chain specific); Jackson ImmunoResearch; West Grove, Pa.) was added to the IgA plates at a dilution of 1:1000 in BSA-PBS. For IgG reactivity, alkaline phosphatase conjugated secondary antibody (goat anti-human IgG (γ-chain specific); Jackson ImmunoResearch) was added. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM MgCl$_2$, 0.01 M Tris, pH 8.6, was added at 100 µl/well, and color allowed to develop for one hour. The plates were then analyzed at 405 nm. Anti-I2 antibody positive reactivity was defined as reactivity greater than two standard deviations above the mean reactivity obtained with control (normal) sera analyzed at the same time as the test samples.

For histological analysis, rabbit anti-I2 antibodies were prepared using purified GST-I2 fusion protein as the immunogen. GST-binding antibodies were removed by adherence to GST bound to an agarose support (Pierce; Rockford, Ill.), and the rabbit sera validated for anti-I2 immunoreactivity by ELISA analysis. Slides were prepared from paraffin-embedded biopsy specimens from test samples and normal controls. Hematoxylin and eosin staining were performed, followed by incubation with I2-specific antiserum. Binding of antibodies was detected with peroxidase-labeled anti-rabbit secondary antibodies (Pierce). The assay was optimized to maximize the signal to background and the distinction between disease and control populations.

Example 4

Determination of Anti-OmpC Antibody Levels

This example illustrates the preparation of OmpC protein and an analysis of anti-OmpC antibody levels in a sample using ELISA.

The following protocol describes the purification of OmpC protein using spheroplast lysis. OmpF/OmpA-mutant *E. coli* were inoculated from a glycerol stock into 10-20 ml of Luria Bertani broth supplemented with 100 µg/ml streptomycin (LB-Strep; Teknova; Half Moon Bay, Calif.) and cultured vigorously at 37° C. for about 8 hours to log phase, followed by expansion to 1 liter in LB-Strep over 15 hours at 25° C. The cells were harvested by centrifugation. If necessary, cells are washed twice with 100 ml of ice cold 20 mM Tris-Cl, pH 7.5. The cells were subsequently resuspended in ice cold spheroplast forming buffer (20 mM Tris-Cl, pH 7.5; 20% sucrose; 0.1M EDTA, pH 8.0; 1 mg/ml lysozyme), after which the resuspended cells were incubated on ice for about 1 hour with occasional mixing by inversion. If required, the spheroplasts were centrifuged and resuspended in a smaller volume of spheroplast forming buffer (SFB). The spheroplast pellet was optionally frozen prior to resuspension in order to improve lysis efficiency. Hypotonic buffer was avoided in order to avoid bursting the spheroplasts and releasing chromosomal DNA, which significantly decreases the efficiency of lysis.

The spheroplast preparation was diluted 14-fold into ice cold 10 mM Tris-Cl, pH 7.5 containing 1 mg/ml DNaseI and was vortexed vigorously. The preparation was sonicated on ice 4×30 seconds at 50% power at setting 4, with a pulse "On time" of 1 second, without foaming or overheating the sample. Cell debris was pelleted by centrifugation and the supernatant was removed and clarified by centrifugation a second time. The supernatant was removed without collecting any part of the pellet and placed into ultracentrifuge tubes. The tubes were filled to 1.5 mm from the top with 20 mM Tris-Cl, pH 7.5. The membrane preparation was pelleted by ultracentrifugation at 100,000×g for 1 hr at 4° C. in a Beckman SW 60 swing bucket rotor. The pellet was resuspended by homogenizing into 20 mM Tris-Cl, pH 7.5 using a 1 ml pipette tip and squirting the pellet closely before pipetting up and down for approximately 10 minutes per tube. The material was extracted for 1 hr in 20 mM Tris-Cl, pH 7.5 containing 1% SDS, with rotation at 37° C. The preparation was transferred to ultracentrifugation tubes and the membrane was pelleted at 100,000×g. The pellet was resuspended by homogenizing into 20 mM Tris-Cl, pH 7.5 as before. The membrane preparation was optionally left at 4° C. overnight.

OmpC was extracted for 1 hr with rotation at 37° C. in 20 mM Tris-Cl, pH 7.5 containing 3% SDS and 0.5 M NaCl. The material was transferred to ultracentrifugation tubes and the membrane was pelleted by centrifugation at 100,000×g. The supernatant containing extracted OmpC was then dialyzed against more than 10,000 volumes to eliminate high salt content. SDS was removed by detergent exchange against 0.2% Triton. Triton was removed by further dialysis against 50 mM Tris-Cl. Purified OmpC, which functions as a porin in its trimeric form, was analyzed by SDS-PAGE. Electrophoresis at room temperature resulted in a ladder of bands of about 100 kDa, 70 kDa, and 30 kDa. Heating for 10-15 minutes at 65-70° C. partially dissociated the complex and resulted in only dimers and monomers (i.e., bands of about 70 kDa and 30 kDa). Boiling for 5 minutes resulted in monomers of 38 kDa.

The OmpC direct ELISA was performed essentially as follows. Plates (USA Scientific; Ocala, Fla.) were coated overnight at 4° C. with 100 μl/well OmpC at 0.25 μg/ml in borate buffered saline, pH 8.5. After three washes in 0.05% Tween 20 in phosphate buffered saline (PBS), the plates were blocked with 150 μl/well of 0.5% bovine serum albumin in PBS, pH 7.4 (BSA-PBS) for 30 minutes at room temperature. The blocking solution was then replaced with 100 μl/well of test serum or normal control serum, diluted 1:100. The plates were then incubated for 2 hours at room temperature and washed as before. Alkaline phosphatase-conjugated goat anti-human IgA (α-chain specific), or IgG (γ-chain specific) (Jackson ImmunoResearch; West Grove, Pa.) was added to the plates at a dilution of 1:1000 in BSA-PBS. The plates were incubated for 2 hours at room temperature before washing three times with 0.05% Tween 20/PBS followed by another three washes with Tris buffered normal saline, pH 7.5. Substrate solution (1.5 mg/ml disodium p-nitrophenol phosphate (Aresco; Solon, Ohio) in 2.5 mM MgCl$_2$, 0.01M Tris, pH 8.6) was added at 100 μl/well, and color was allowed to develop for one hour. The plates were then analyzed at 405 nm. IgA OmpC positive reactivity was defined as reactivity greater than two standard deviations above the mean reactivity obtained with control (normal) sera analyzed at the same time as the test samples.

Example 5

Determination of the Presence of pANCA

This example illustrates an analysis of the presence or absence of pANCA in a sample using an immunofluorescence assay as described, e.g., in U.S. Pat. Nos. 5,750,355 and 5,830,675. In particular, the presence of pANCA is detected by assaying for the loss of a positive value (e.g., loss of a detectable antibody marker and/or a specific cellular staining pattern as compared to a control) upon treatment of neutrophils with DNase.

Neutrophils isolated from a sample such as serum are immobilized on a glass side according to the following protocol:
1. Resuspend neutrophils in a sufficient volume of 1× Hanks' Balanced Salt Solution (HBSS) to achieve about 2.5×10$^6$ cells per ml.
2. Use a Cytospin3 centrifuge (Shandon, Inc.; Pittsburgh, Pa.) at 500 rpm for 5 minutes to apply 0.01 ml of the resuspended neutrophils to each slide.
3. Fix neutrophils to slide by incubating slides for 10 minutes in sufficient volume of 100% methanol to cover sample. Allow to air dry. The slides may be stored at −20° C.

The immobilized, fixed neutrophils are then treated with DNase as follows:
1. Prepare a DNase solution by combining 3 units of Promega RQ1™ DNase (Promega; Madison, Wis.) per ml buffer containing 40 mM of TRIS-HCl (pH 7.9), 10 mM of sodium chloride, 6 mM magnesium chloride, and 10 mM calcium chloride.
2. Rinse slides prepared using the above protocol with about 100 ml phosphate buffered saline (pH 7.0-7.4) for 5 minutes. Incubate immobilized neutrophils in 0.05 ml of DNase solution per slide for about 30 minutes at 37° C. Wash the slides three times with about 100-250 ml phosphate buffered saline at room temperature. The DNase reaction carried out as described herein causes substantially complete digestion of cellular DNA without significantly altering nuclear or cellular neutrophil morphology.

Next, an immunofluorescence assay is performed on the DNase-treated, fixed neutrophils according to the following protocol:
1. Add 0.05 ml of a 1:20 dilution of human sera in phosphate buffered saline to slides treated with DNase and to untreated slides. Add 0.05 ml phosphate buffered saline to clean slides as blanks. Incubate for about 0.5 to 1.0 hour at room temperature in sufficient humidity to minimize volume loss.
2. Rinse off sera by dipping into a container having 100-250 ml phosphate buffered saline.
3. Soak slide in phosphate buffered saline for 5 minutes. Blot lightly.
4. Add 0.05 ml goat F(ab')$_2$ anti-human IgG(μ)-FITC (Tago Immunologicals; Burlingame, Calif.), at a 1:1000 antibody:phosphate buffered saline dilution, to each slide. Incubate for 30 minutes at room temperature in sufficient humidity to minimize volume loss.
5. Rinse off antibody with 100-250 ml phosphate buffered saline. Soak slides for 5 minutes in 100-250 ml phosphate buffered saline, then allow to air dry.
6. Read fluorescence pattern on fluorescence microscope at 40×.
7. If desired, any DNA can be stained with propidium iodide stain by rinsing slides well with phosphate buffered saline at room temperature and stain for 10 seconds at room temperature. Wash slide three times with 100-250 ml phosphate buffered saline at room temperature and mount cover slip.

The immunofluorescence assay described above can be used to determine the presence of pANCA in DNase-treated, fixed neutrophils, e.g., by the presence of a pANCA reaction in control neutrophils (i.e., fixed neutrophils that have not been DNase-treated) that is abolished upon DNase treatment or by the presence of a pANCA reaction in control neutrophils that becomes cytoplasmic upon DNase treatment.

Example 6

Statistical Algorithm for Ruling Out IBD

This example illustrates a statistical algorithm that was developed to classify a sample as a non-IBD sample or as an IBD sample using a panel of serological markers.

A large cohort of serological samples from normal and diseased patients was used in this study and the levels and/or presence of a panel of various anti-bacterial antibody markers were measured to assess the capability of the panel to distinguish between IBD and non-MD samples. The training and testing set used for developing a statistical algorithm to rule out IBD (i.e., predict non-IBD) contained a total of 1,801 samples (474 healthy controls, 248 IBS, 543 Crohn's disease, and 23 ulcerative colitis) with an IBD prevalence of 59%. The training set consisted of about 70%-90% of the training and testing set while the test set consisted of about 10%-30% of the training and testing set. The panel of serological markers included at least one of the following: ANCA, ASCA-IgA, ASCA-IgG, anti-OmpC antibodies, anti-flagellin antibodies (e.g., anti-Cbir-1 antibodies), and pANCA. The levels of ANCA, ASCA-IgA, ASCA-IgG, anti-OmpC antibodies, and anti-flagellin antibodies were determined by ELISA. Indirect immunofluorescence microscopy was used to determine whether a sample was positive or negative for pANCA.

In this study, a novel approach was developed that uses a hybrid of different learning statistical classifiers (e.g., random forests, classification and regression trees (CART), neural networks (NN), support vector machines (SVM), and the like) to classify a sample as an IBD sample or as a non-IBD sample based upon the levels and/or presence of a panel of serological markers. These learning statistical classifiers use multivariate statistical methods that can adapt to complex data and make decisions based strictly on the data presented, without the constraints of regular statistical classifiers. In particular, a combinatorial approach that makes use of multiple discriminant functions by analyzing markers with more than one learning statistical classifier in tandem was created to further improve the overall accuracy of ruling out IBD in a sample from an individual suspected of having IBS. The model that performed with the greatest accuracy used a statistical algorithm that was derived from a combination of random forests and NN.

Figure 3:
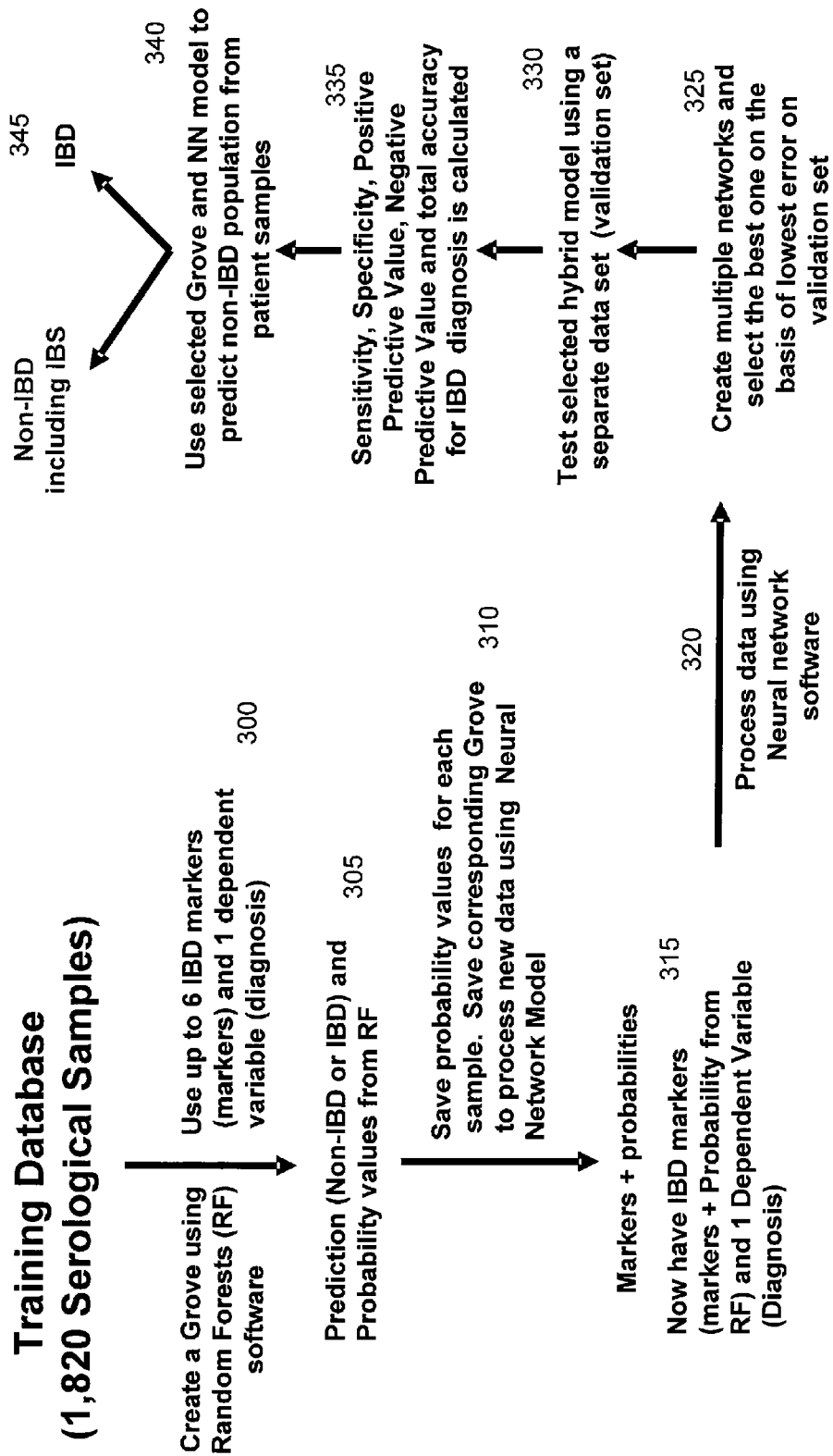
FIG. 3 illustrates a flowchart describing a statistical algorithm of the present invention for ruling out IBD.

As shown in FIG. 3, the results from each of the markers ("Markers") and a dependent variable ("Diagnosis"; 0=Normal, 1=MD) were input into the RandomForests software of Salford Systems to create a grove (300). The grove was then used to obtain prediction (i.e., IBD or non-IBD) and probability values (305). The grove and probability values for each sample were saved (310). The probability values calculated from random forests ("Probabilities") were next combined with the results from each of the markers and the dependent variable (315) and processed using the NN software module of Statistica Data Miner Version 7.1 (320). Multiple networks were created and the best model was selected on the basis of the lowest error on a validation set containing a total of 341 samples (199 healthy controls, 96 IBS, 23 Crohn's disease, and 23 ulcerative colitis) with an IBD prevalence of 15% (325). Different samples were used in the validation set and in the training and testing set. The best model was then validated using the validation set (330). Clinical parameters such as sensitivity, specificity, positive predictive value (PPV), negative predictive value (NPV), and overall accuracy for diagnosing IBD were calculated (335). The selected grove and NN hybrid model was then used to predict the non-IBD population from patient samples (340). As a result, this hybrid model is particularly useful for classifying samples as IBD samples or as non-IBD samples that could include IBS (345). Assay precision was calculated from the confusion matrix produced by the NN program using Microsoft Excel.

Table 1 below shows the prediction accuracy of various grove and NN hybrid models created using a three-marker system consisting of ANCA, ASCA-IgG, and anti-OmpC antibodies. In particular, this table illustrates that 97% of all IBD samples present in the test set were classified as non-IBD samples (see, NPV column).

TABLE 1

| Model | Sensitivity | Specificity | PPV | NPV |
|---|---|---|---|---|
| 1 | 85% | 80% | 39% | 97% |
| 2 | 85% | 90% | 57% | 97% |
| 3 | 87% | 75% | 35% | 97% |
| 4 | 85% | 82% | 42% | 97% |
| 5 | 85% | 87% | 51% | 97% |
| 6 | 85% | 85% | 48% | 97% |
| 7 | 83% | 89% | 54% | 97% |
| 8 | 85% | 82% | 42% | 97% |
| 9 | 85% | 82% | 42% | 97% |
| 10 | 85% | 86% | 49% | 97% |
| 11 | 85% | 85% | 48% | 97% |
| 12 | 85% | 85% | 48% | 97% |
| 13 | 85% | 82% | 42% | 97% |
| 14 | 85% | 88% | 53% | 97% |
| 15 | 85% | 83% | 43% | 97% |
| 16 | 85% | 82% | 42% | 97% |
| 17 | 85% | 83% | 44% | 97% |
| 18 | 85% | 89% | 55% | 97% |
| 19 | 85% | 88% | 53% | 97% |
| 20 | 85% | 82% | 42% | 97% |

Hybrid models 2, 3, 4, 5, and 18 in Table 1 above produced the best overall set of clinical parameters. Such hybrid models, when used in combination with assays to rule out other diseases and disorders having IBS-like symptoms, can classify patient samples into one of two groups: (1) a group containing samples associated with diseases and disorders having a similar clinical presentation as IBS; and (2) a non-IBD, IBS-enriched group containing normal and IBS samples.

Example 7

Statistical Algorithm for Ruling in IBS

This example illustrates a statistical algorithm that was developed to classify a non-IBD sample as an IBS sample or as a non-IBS sample using a panel of serological markers.

Another cohort of serological samples from normal and diseased patients was used in this study and the levels and/or presence of a panel of various anti-bacterial antibody markers were measured to assess the capability of the panel to distinguish between IBS and non-IBD samples. The training and testing set used for developing a statistical algorithm to rule in IBS (i.e., predict IBS) contained a total of 722 samples (475 healthy controls and 247 IBS) with an IBS prevalence of 34%. The training set consisted of about 70%-90% of the training and testing set while the test set consisted of about 10%-30% of the training and testing set. The panel of serological markers included at least one of the following: ANCA, ASCA-IgA, ASCA-IgG, anti-OmpC antibodies, anti-flagellin antibodies (e.g., anti-Cbir-1 antibodies), and pANCA. In certain instances, the panel of serological markers further comprised one or more of the IBS markers described above.

Figure 4:
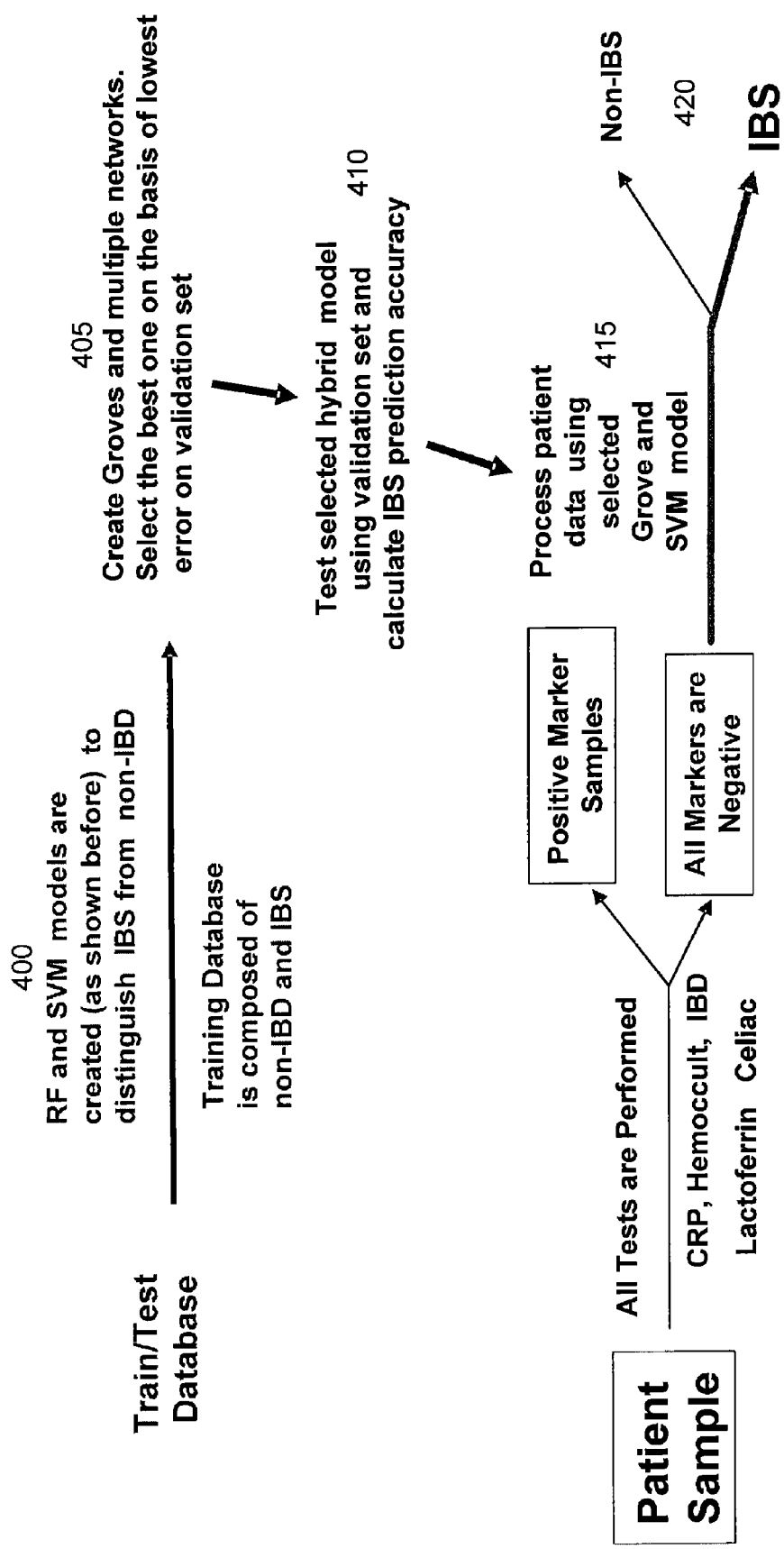
FIG. 4 illustrates a flowchart describing a statistical algorithm of the present invention for ruling in IBS.

As shown in FIG. 4, random forest and neural network (NN) or support vector machine (SVM) models were generated as described in Example 6 to distinguish IBS samples from non-IBD samples (400). The random forest model was used to create a grove, which was then processed using an NN or SVM model to create multiple networks (405). The best model was selected on the basis of the lowest error on a validation set containing a total of 304 samples (207 healthy controls and 97 IBS) with an IBD prevalence of 32%. Different samples were used in the validation set and in the training and testing set. The best model was then validated using the validation set (410). Clinical parameters such as sensitivity, specificity, positive predictive value (PPV), and negative predictive value (NPV) were calculated to determine the accuracy of the hybrid model for predicting IBS.

Table 2 below shows the prediction accuracy of various grove and NN hybrid models created using a three-marker system consisting of ANCA, ASCA-IgG, and anti-OmpC antibodies. In particular, this table illustrates that the accuracy of the hybrid model for ruling in IBS was greater than 80% (see, Accuracy column).

TABLE 2

| Model | Sensitivity | Specificity | PPV | NPV | Accuracy |
|---|---|---|---|---|---|
| 21 | 79% | 84% | 70% | 89% | 82% |
| 22 | 79% | 87% | 75% | 90% | 84% |
| 23 | 79% | 86% | 73% | 90% | 84% |
| 24 | 77% | 89% | 77% | 89% | 85% |
| 25 | 80% | 85% | 73% | 90% | 84% |
| 26 | 79% | 87% | 75% | 90% | 84% |
| 27 | 80% | 86% | 74% | 90% | 84% |
| 28 | 80% | 85% | 72% | 90% | 83% |
| 29 | 79% | 86% | 73% | 90% | 84% |
| 30 | 77% | 86% | 73% | 89% | 83% |
| 31 | 80% | 86% | 74% | 90% | 84% |
| 32 | 79% | 87% | 75% | 90% | 84% |
| 33 | 79% | 83% | 70% | 89% | 82% |
| 34 | 78% | 85% | 72% | 89% | 83% |
| 35 | 80% | 86% | 73% | 90% | 84% |
| 36 | 80% | 86% | 73% | 90% | 84% |
| 37 | 76% | 89% | 78% | 89% | 85% |
| 38 | 79% | 85% | 72% | 89% | 83% |
| 39 | 80% | 86% | 74% | 90% | 84% |
| 40 | 79% | 86% | 73% | 90% | 84% |
| 522 | 82% | 86% | 75% | 91% | 85% |

Hybrid models 27, 31, 39, and 522 in Table 2 above produced the best overall set of clinical parameters. Such hybrid models can be used to process those samples in which other disease and disorders with IBS-like symptoms have been ruled out (415) to classify them as either IBS samples or as non-IBS samples (420).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for classifying whether a sample from an individual not having inflammatory bowel disease (IBD) is associated with irritable bowel syndrome (IBS), the method comprising:
   (a) measuring a concentration level of at least one marker in said sample, wherein said at least one marker comprises an anti-flagellin antibody; and
   (b) applying a combination of at least two learning statistical classifier systems to the measured concentration level of said at least one marker to classify said sample as an IBS sample or as a non-IBS sample.

2. The method of claim 1, wherein said at least one marker further comprises an anti-neutrophil cytoplasmic antibody (ANCA), an anti-*Saccharomyces cerevisiae* immunoglobulin A antibody (ASCA-IgA), an anti-*Saccharomyces cerevisiae* immunoglobulin G antibody (ASCA-IgG), an anti-outer membrane protein C (anti-OmpC) antibody, an anti-I2 antibody, a perinuclear anti-neutrophil cytoplasmic antibody (pANCA), or combinations thereof.

3. The method of claim 1, wherein said sample is selected from the group consisting of serum, plasma, whole blood, and stool.

4. The method of claim 1, wherein said combination of at least two learning statistical classifier systems comprises a decision/classification tree in combination with a neural network or support vector machine.

5. The method of claim 4, wherein said decision/classification tree is a classification and regression tree (C&RT) or a random forest.

6. The method of claim 4, wherein said combination of at least two learning statistical classifier systems is used in tandem.

7. The method of claim 6, wherein said decision/classification tree is first used to generate a probability value based upon the level of said at least one marker.

8. The method of claim 7, wherein said neural network or support vector machine is then used to classify IBS in said sample based upon said probability value and the level of said at least one marker.

9. The method of claim 1, wherein said combination of at least two learning statistical classifier systems classifies said sample with a specificity of at least 80%.

10. The method of claim 1, wherein said combination of at least two learning statistical classifier systems classifies said sample with an overall accuracy of at least 60%.

11. The method of claim 1, wherein the concentration level of said at least one marker is measured by assaying said sample with an immunoassay.

12. The method of claim 11, wherein said immunoassay is an enzyme-linked immunosorbent assay (ELISA).

13. The method of claim 1, wherein the concentration level of anti-flagellin antibody is measured by assaying the binding between the anti-flagellin antibody and a flagellin protein or an immunoreactive fragment thereof.

14. The method of claim 13, wherein said flagellin protein comprises Cbir-1 flagellin, flagellin X, flagellin A, flagellin B, immunoreactive fragments thereof, or combinations thereof.

15. The method of claim 1, wherein said method further comprises sending the results from said classification to a clinician.

16. The method of claim 1, wherein said method further provides a diagnosis in the form of a probability that said individual has IBS.

17. The method of claim 1, wherein said IBS is characterized by at least one symptom selected from the group consisting of abdominal pain, abdominal discomfort, change in bowel pattern, loose or more frequent bowel movements, diarrhea, constipation, and a combination thereof.

18. The method of claim 1, wherein said method further comprises administering to said individual a therapeutically effective amount of a drug useful for treating one or more symptoms associated with IBS if said sample is classified as an IBS sample.

19. The method of claim 18, wherein said drug is selected from the group consisting of serotonergic agents, antidepressants, chloride channel activators, guanylate cyclase agonists, antibiotics, opioids, neurokinin antagonists, antispasmodic or anticholinergic agents, belladonna alkaloids, barbiturates, free bases thereof, pharmaceutically acceptable salts thereof, and combinations thereof.

20. The method of claim 1, wherein said anti-flagellin antibody comprises an anti-Cbir-1 flagellin antibody.

* * * * *

SEQUENCE LISTING

```
<160> NUMBER OF SEQ ID NOS: 15

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence:amino acids
      57-89 of alpha2-gliadin, multivalent 33-mer
      peptide substrate for tissue transglutaminase
      (tTG) recognized by anti-gluten antibody

<400> SEQUENCE: 1

Leu Gln Leu Gln Pro Phe Pro Gln Pro Gln Leu Pro Tyr Pro Gln Pro
 1               5                  10                  15

Gln Leu Pro Tyr Pro Gln Pro Gln Leu Pro Tyr Pro Gln Pro Gln Pro
                20                  25                  30

Phe

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 2

Pro Phe Pro Gln Pro Gln Leu Pro Tyr
 1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 3

Pro Gln Pro Gln Leu Pro Tyr Pro Gln
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 4

Pro Gln Leu Pro Tyr Pro Gln Pro Gln
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 5

Pro Tyr Pro Gln Pro Gln Leu Pro Tyr
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 6

Pro Gln Pro Glu Leu Pro Tyr Pro Gln
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 7

Pro Phe Pro Gln Pro Glu Leu Pro Tyr
  1               5

<210> SEQ ID NO 8
<211> LENGTH: 9
<212> TYPE: PRT
<213> ORGANISM: Artificial Sequence
```

-continued

```
<220> FEATURE:
<223> OTHER INFORMATION: Description of Artificial Sequence:anti-gluten
      antibody polypeptide antigen, independently
      selected epitope

<400> SEQUENCE: 8

Pro Gln Gln Ser Phe Pro Gln Gln Gln
 1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 9

Pro Phe Pro Gln Gln Pro Gln Gln Pro Phe Pro
 1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:anti-gluten
      antibody polypeptide antigen, independently
      selected epitope

<400> SEQUENCE: 10

Pro Tyr Pro Gln Pro Glu Leu Pro Tyr
 1               5

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence:mutivalent
      peptide from alpha1-gliadin and alph6-gliadin
      recognized by anti-gluten antibody

<400> SEQUENCE: 11

Gln Pro Gln Pro Phe Pro Pro Gln Leu Pro Tyr Pro Gln Thr Gln Pro
 1               5                  10                  15

Phe Pro Pro Gln Gln Pro Tyr Pro Gln Pro Gln Pro Tyr Pro Gln
                20                  25                  30

Pro Gln

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence:mutivalent
      peptide from B1 hordein recognized by anti-gluten
      antibody

<400> SEQUENCE: 12

Gln Gln Gln Pro Phe Pro Gln Gln Pro Ile Pro Gln Gln Pro Gln Pro
 1               5                  10                  15

Tyr Pro Gln Gln Pro Gln Pro Tyr Pro Gln Gln Pro Phe Pro Pro Gln
                20                  25                  30

Gln Pro Phe
        35
```

```
<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence:mutivalent
      peptide recognized by anti-gluten antibody

<400> SEQUENCE: 13

Gln Pro Phe Pro Gln Pro Gln Gln Thr Phe Pro Gln Gln Pro Gln Leu
 1               5                  10                  15

Pro Phe Pro Gln Gln Pro Gln Gln Pro Phe Pro Gln Pro Gln
            20                  25                  30

<210> SEQ ID NO 14
<211> LENGTH: 59
<212> TYPE: PRT
<213> ORGANISM: Artificial Sequence
<220> FEATURE:
<223> OTHER INFORMATION: Description of Artificial Sequence:mutivalent
      peptide from gamma-gliadin recognized by
      anti-gluten antibody

<400> SEQUENCE: 14

Pro Gln Gln Pro Gln Leu Pro Phe Pro Gln Gln Pro Gln Gln Pro Phe
 1               5                  10                  15

Pro Gln Pro Gln Gln Pro Gln Gln Pro Phe Pro Gln Ser Gln Gln Pro
            20                  25                  30

Gln Gln Pro Phe Pro Gln Pro Gln Gln Gln Phe Pro Gln Pro Gln Gln
        35                  40                  45

Pro Gln Gln Ser Phe Pro Gln Gln Gln Pro
        50                  55

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence:mutivalent
      peptide recognized by anti-gluten antibody

<400> SEQUENCE: 15

Gln Pro Phe Pro Gln Pro Gln Gln Pro Thr Pro Ile Gln Pro Gln Gln
 1               5                  10                  15

Pro Phe Pro Gln Arg Pro Gln Gln Pro Phe Pro Gln Pro Gln
            20                  25                  30
```